United States Patent [19]

Bernady et al.

[11] 4,006,179
[45] Feb. 1, 1977

[54] 1-ALKOXIMINO-2-(ω-SUBSTITUTED ALKYL)-2-CYCLOPENTENES

[75] Inventors: Karel Francis Bernady, Suffern; John Frank Poletto, Nanuet, both of N.Y.; Martin Joseph Weiss, Oradell, N.J.

[73] Assignee: American Cyanamid Company, Stamford, Conn.

[22] Filed: Feb. 24, 1975

[21] Appl. No.: 552,686

Related U.S. Application Data

[60] Division of Ser. No. 480,908, June 19, 1974, which is a division of Ser. No. 335,842, Feb. 26, 1973, Pat. No. 3,836,581, which is a continuation-in-part of Ser. No. 208,951, Dec. 16, 1971, abandoned.

[52] U.S. Cl. .......................... 260/468 J; 260/514 J
[51] Int. Cl.$^2$ .................. C07C 61/38; C07C 69/74
[58] Field of Search ........ 260/514 D, 514 J, 468 D, 260/468 J

[56] References Cited

UNITED STATES PATENTS

| | | | |
|---|---|---|---|
| 3,432,541 | 3/1969 | Bagle et al. | 260/468 |
| 3,847,966 | 11/1974 | Pike | 260/468 |
| 3,897,483 | 7/1975 | Bernardy et al. | 260/488 |

*Primary Examiner*—Robert Gerstl
*Attorney, Agent, or Firm*—Denis A. Polyn

[57] ABSTRACT

This disclosure describes certain 1-alkoximino-2-(ω-substituted-alkyl)-2-cyclopentenes useful as intermediates for the preparation of homologues, analogues, congeners, and derivatives of 9-oxo-13-trans-prostenoic acid and of 9-hydroxy-13-trans-prostenoic acid which have antimicrobial activity and prostaglandin-like hypotensive activity.

3 Claims, No Drawings

1-ALKOXIMINO-2-(ω-SUBSTITUTED ALKYL)-2-CYCLOPENTENES

CROSS REFERENCE TO RELATED APPLICATIONS

This application is a division of our copending application Ser. No. 480,908, filed June 19, 1974, which is a division of our application Ser. No. 335,842, filed Feb. 26, 1973, now U.S. Pat. No. 3,836,581, which is a continuation-in-part of our application Ser. No. 208,951, filed Dec. 16, 1971, now abandoned.

BRIEF SUMMARY OF THE INVENTION

This invention relates to new organic compounds, and more particularly, is concerned with novel intermediates for a class of compounds related to the natural prostaglandins. The novel compounds of the present invention may be represented by the following general formula:

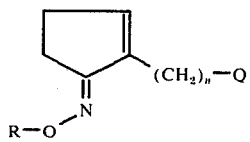

wherein n is an integer from 3 to 8, inclusive; R is a lower alkyl group having up to four carbon atoms; and Q is selected from the group consisting of hydroxy, lower alkanesulfonyloxy, p-toluenesulfonyloxy, chloro, bromo, iodo, lower acyloxy, cyano, carboxy, lower carboalkoxy, dicarboxymethyl, di(lower carboalkoxy)methyl, and moieties of the formulae:

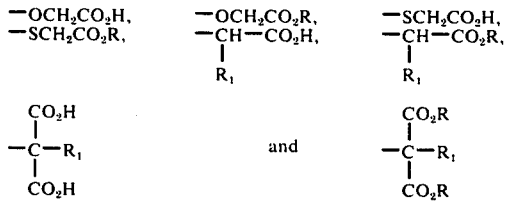

wherein R is a lower alkyl group and $R_1$ is selected from the group consisting of lower alkyl, fluoro and phenyl. Suitable lower alkyl, lower alkane, lower acyloxy, and lower carboalkoxy groups contemplated by the present invention are those having up to four carbon atoms such as, for example, methyl, ethyl, secbutyl, methane, ethane, n-propane, acetyloxy, propionyloxy, isobutyryloxy, carbomethoxy, carboethoxy, carbo-n-propoxy, and the like.

DETAILED DESCRIPTION OF THE INVENTION

The prostaglandins are a family of closely related compounds which have been obtained from various animal tissues, and which stimulate smooth muscle, lower arterial blood pressure, antagonize epinephrine-induced mobilization of free fatty acids, and have other pharmacological and autopharmacological effects in mammals. See Bergstrom et al., J. Biol. Chem. 238, 3555 (1963) and Horton, Experienta 21, 113 (1965) and references cited therein. All of the so-called natural prostaglandins are derivatives of prostanoic acid:

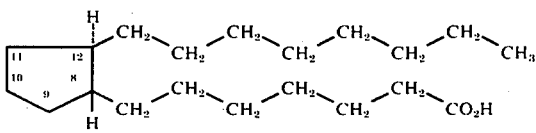

The hydrogen atoms attached to C-8 and C-12 are in trans configuration. The novel compounds of the present invention are useful as intermediates for the preparation of homologues, analogues, congeners, and derivatives of 9-oxo-13-trans-prostenoic acid and of 9-hydroxy-13-trans-prostenoic acid having antimicrobial activity and prostaglandin-like hypotensive activity as is set forth hereinafter.

The novel compounds of the present invention may be readily prepared from 2-carbethoxycyclopentanone in accordance with the reaction schemes set forth in Flowsheets A through E. In particular, the requisite 2-(ω-carbethoxyalkyl)cyclopent-2-en-1-one intermediates (VIII) may be prepared in accordance with the following reaction scheme:

FLOWSHEET A

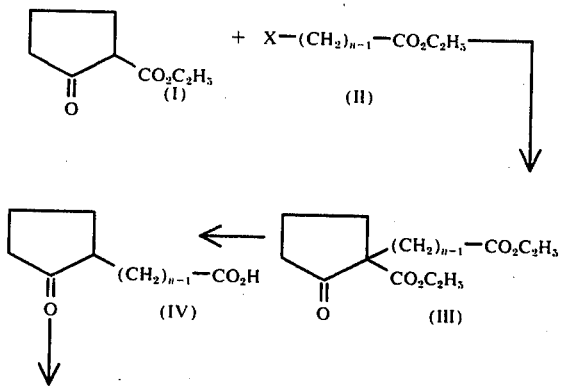

FLOWSHEET A-continued

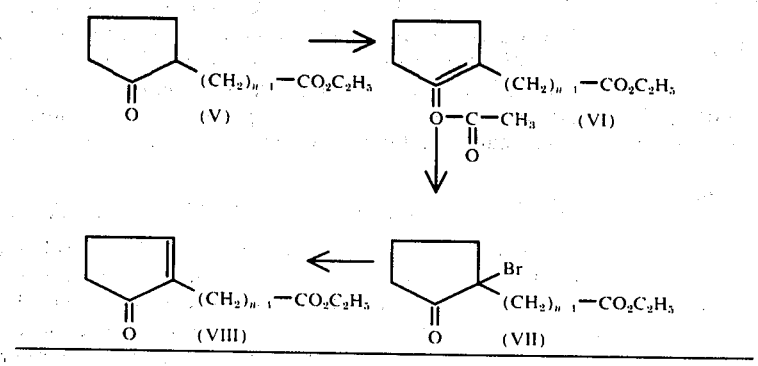

wherein n is as hereinabove defined and X is iodo or bromo. In accordance with this reaction scheme, the cyclopent-2-en-1-ones (VIII) are developed by first converting 2-carbethoxycyclopentanone (I) to the sodium enolate thereof by means of sodium hydride in dimethoxyethane and then treating the sodium enolate with an ethyl ω-haloalkanoate (II). There is thus obtained the corresponding 2-carbethoxy-2-(ω-carbethoxyalkyl)cyclopentanone (III) which is then hydrolyzed and decarboxylated to afford the 2-(ω-carboxyalkyl)cyclopentanone (IV). This acid is then esterified with ethanol whereby the 2-(ω-carbethoxyalkyl)cyclopentanone (V) is obtained. The reaction conditions for carrying out the above sequence of reactions are well known in the art. The conversion of the cyclopentanone (V) to the enol acetate (VI) is effected by heating with acetic anhydride in the presence of p-toluenesulfonic acid. Preparation of the enol acetate (VI) usually requires heating for a period of from about eight to thirty-six hours. During this period, it is preferable to allow by-product acetic acid to distill out in order to force the reaction to completion. The bromination of the enol acetates (VI) to the 2-bromocyclopentanones (VII) is preferably carried out in a two phase system as follows. A solution of bromine in chloroform is added to a rapidly stirred mixture of a solution of the enol acetate (VI) in chloroform and an aqueous solution of an acid acceptor such as calcium carbonate or soda ash. This addition is carried out at 0°–5° C. over a period of about half an hour, stirring is continued for an additional period of about half an hour to a few hours, and the product (VII) is then isolated by standard procedures. The dehydrobromination of the 2-bromocyclopentanones (VII) is preferably carried out in dimethylformamide with a mixture of lithium bromide and lithium carbonate at the reflux temperature for a period of about 30 minutes to an hour or so. The so formed cyclopent-2-en-1-ones (VIII) are also isolated by standard procedures well known in the art.

The required cyclopent-2-en-1-one intermediates wherein the side-chain has a substituent $R_1$ alpha to the carboxy or carboalkoxy function may be prepared in accordance with the following reaction scheme:

FLOWSHEET B

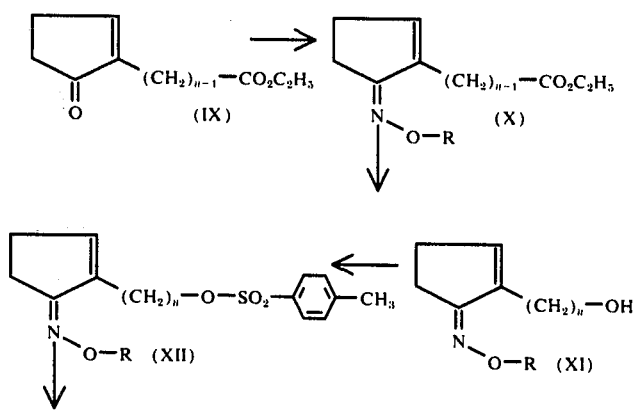

FLOWSHEET B-continued

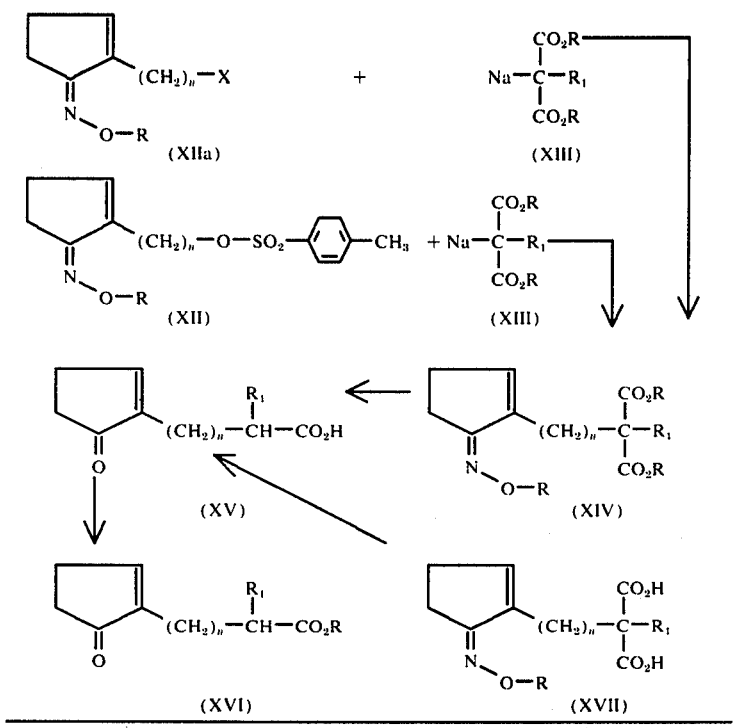

wherein n and R and $R_1$ are as hereinabove defined; and X is chloro, bromo or iodo. In accordance with this reaction scheme, the 2-(ω-carbethoxyalkyl)cyclopent-2-en-1-ones (IX) are converted to the corresponding 1-alkoximino-2-(ω-carbethoxyalkyl)-2-cyclopentenes (X) by treatment with an alkoxyamine. With the ring carbonyl function thus blocked it is possible to effect a preferential reduction of the ester group by treatment with diisobutylaluminum hydride. The resulting alcohol (XI) is converted to a tosylate derivative (XII), which undergoes displacement on treatment with the sodium salt of a dialkyl substituted malonate (XIII) to provide the disubstituted malonate derivatives (XIV). Sometimes it is preferable to conduct the malonate displacement on a halide derivative (XIIa), which is readily preparable from the tosylate (XII) by displacement with chloride, bromide or iodide. Among the substituted dialkyl malonates (XIII) which can be utilized are diethyl ethylmalonate, diethyl fluoromalonate and diethyl phenylmalonate. Hydrolysis and decarboxylation as well as concomittant cleavage of the alkoximino blocking group provides the desired 2-(ω-carboxy-α-substituted alkyl)cyclopent-2-en-1-ones (XV), which are readily converted to the corresponding ester (XVI) by the usual Fisher procedure or via the acid chloride. Hydrolysis without decarboxylation and concomittant cleavage of the alkoximino blocking group provides the intermediate 1-alkoximino-2-(ω-dicarboxy-α-substituted-lower alkyl)-2-cyclopentenes (XVII). These dicarboxylic acids can be decarboxylated to the corresponding alkoximino monocarboxylic acid; alkoxime hydrolysis then provides (XV).

The requisite 2-(ω-carboalkoxy-3-oxa-alkyl)cyclopent-2-en-1-ones (XXIII) and 2-(ω-carboalkoxy-3-thia-alkyl)cyclopent-2-en-1-ones (XXVII) may be prepared in accordance with the reaction scheme of Flowsheet C, wherein n and R are as hereinbefore defined.

FLOWSHEET C

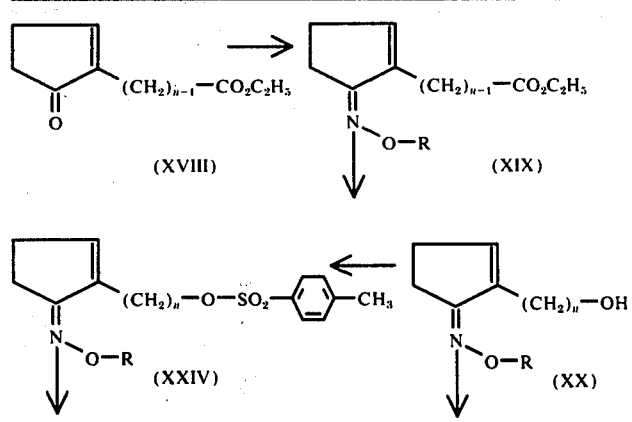

FLOWSHEET C-continued

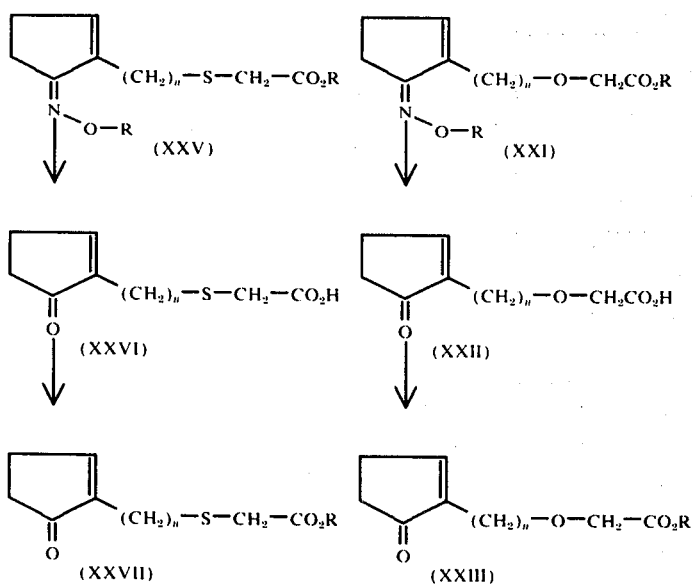

In accordance with the reaction scheme shown in Flowsheet C, for the preparation of the oxa derivative (XXIII), an appropriate 2-(ω-carbethoxyalkyl)cyclopent-2-en-1-one (XVIII) is converted to the corresponding alkoxime (XIX), the ester function of which is then preferentially reduced with diisobutylaluminum hydride to afford the alkoxime alcohol (XX). The alcohol (XX) is converted on treatment with n-butyl lithium to the lithio alcoholate, which then is O-alkylated by reaction with an alkyl bromoacetate to provide (XXI). Hydrolysis with acetone-aqueous hydrochloric acid furnishes the deblocked keto-acid (XXII), which is then re-esterfied with an alkanol in the presence of p-toluenesulfonic acid to give the required 2-(ω-carboalkoxy-3-oxa-alkyl)cyclopent-2-en-1-one (XXIII). O-Alkylation can also be accomplished by treatment of the lithio alcoholate of (XX) with the sodium or other metal salt of chloroacetic acid, in which case the free carboxylix acid corresponding to ester (XXI) is obtained. Hydrolysis as for (XXI) provides the keto acid (XXII).

The preparation of the thia derivatives (XXVII), proceeds from the intermediate alcohol (XX), which after conversion to the tosylate intermediate (XXIV) and reaction with the sodium salt of an alkyl mercaptoacetate furnishes intermediate (XXV). Deblocking of XXV with acetone-aqueous hydrochloric acid provides the keto-acid (XXVI), which on re-esterification with an alkanol gives the required 2-(ω-carboalkoxy-3-thia-alkyl)cyclopent-2-en-1-ones (XXVII).

By the procedure outlined in Flowsheet D below (wherein n and R are as hereinabove defined), it is also possible to homologate the original side chain by one or two carbon atoms. Thus, the 1-alkoximino-2-(ω-hydroxyalkyl)cyclopentene (XXVIII) prepared as described above (compound XX in Flowsheet C and compound XI in Flowsheet B) is converted to the mesylate (XXIX), which on treatment with cyanide ion undergoes displacement of the mesyloxy function to give nitrile (XXX), alkaline hydrolysis of

FLOWSHEET D

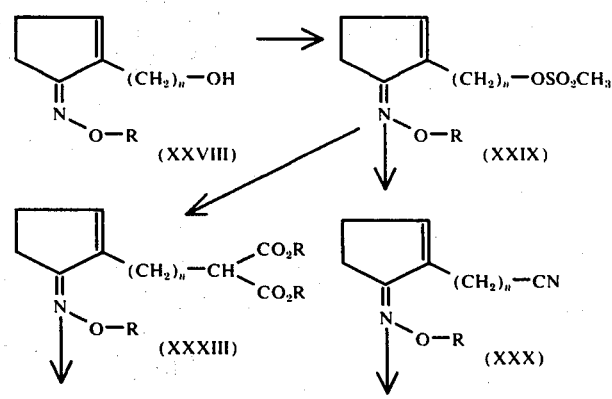

FLOWSHEET D-continued

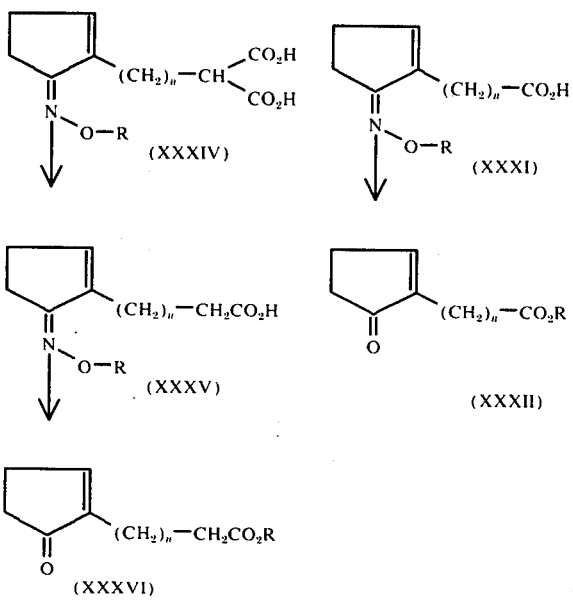

which provides acid (XXXI). The alkoximino group is then cleaved with acid and the carboxylic acid function is esterified to provide cyclopentenone (XXXII) bearing a side chain homologated by one carbon atom relative to cyclopentenone (XVIII) of Flowsheet C.

Two carbon homologation to (XXXVI) is achieved via reaction of mesylate (XXIX) with a dialkyl sodio malonate to give (XXXIII), which is hydrolyzed to the substituted malonic acid (XXXIV) and decarboxylated to (XXXV). Cleavage of the alkoximino function followed by esterification provides the desired (XXXVI).

The mono-substituted malonate (XXXIII) of Flowsheet D also can be utilized for the preparation of certain of the compounds of this invention wherein the carboalkoxy group has an α-substituent. Thus, malonate (XXXIII) is converted to a sodio salt by treatment with sodium hydride, sodium alkoxide, or the like. Reaction of the salt with lower alkylating agents, diphenyliodonium halides, or perchloryl fluoride results in the introduction of lower alkyl, phenyl, or fluoro groups, respectively, to give compound (XIV) of Flowsheet B wherein $R_1$ is lower alkyl, phenyl, or fluoro.

An alternate preparation of the key 2-(ω-hydroxyalkyl)-cyclopent-2-en-1-one alkoxime (XLVI) (XI, XX, and XXVIII in Flowsheets B, C, and D, respectively) is available according to the sequence of the following Flowsheet E, wherein n, R and X are as hereinabove defined. This is essentially the method of Flowsheet A except that 2-carbethoxycyclopentanone (XXXVII) is alkylated with a 1-halo-ω-acyloxyalkane (XXXVIII) to give (XXXIX). This step is followed by decarbalkoxylation, enol alkanoate formation, bromination and dehydrobromination to provide the 2-(ω-alkanoyloxyalkyl)cyclopent-2-en-1-one (XLIV), which is then converted to the alkoxime (XLV). De-0-acylation of (XLV) provides the free alcohol (XLVI).

FLOWSHEET E

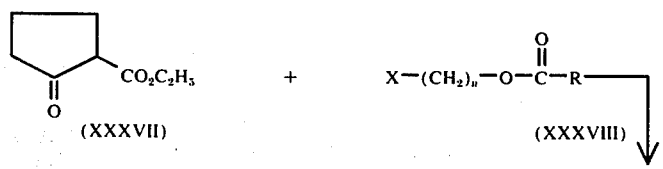

FLOWSHEET E-continued

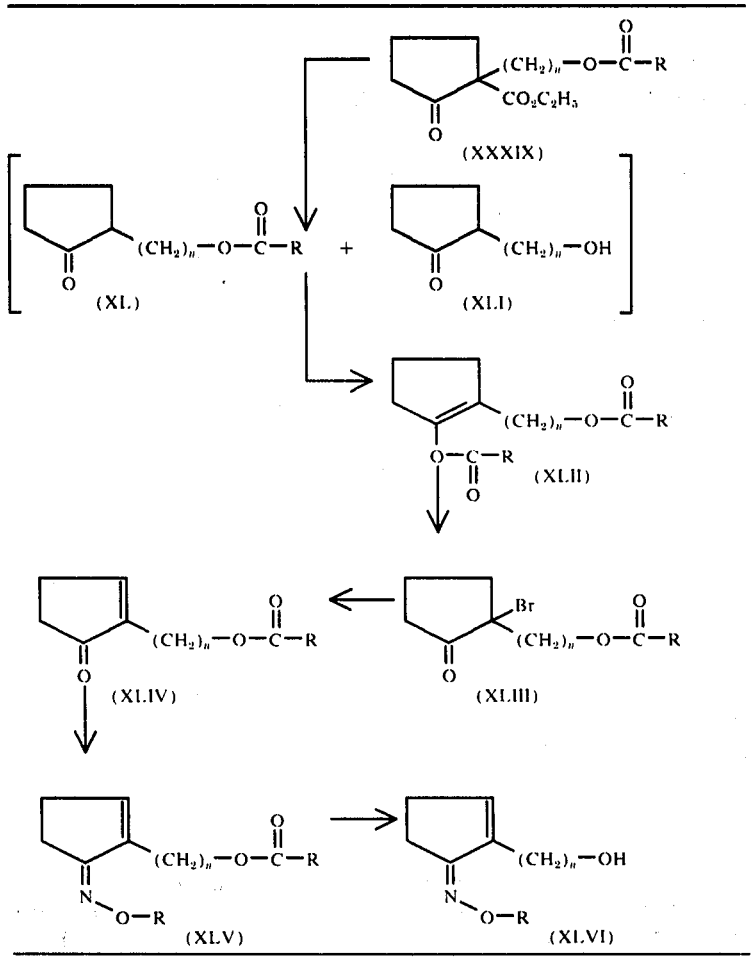

The conjugate 1,4-addition of an alanate salt (XLIX and L) as set forth in the following Flowsheet F: (XLVIII) to a 2-substituted cyclopent-2-en-1-one

FLOWSHEET F

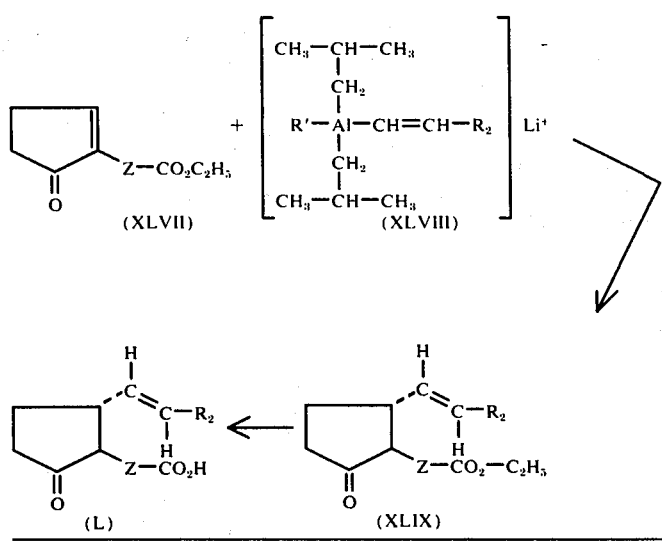

(XLVII), obtained by hydrolysis of the corresponding 1-alkoximino derivatives of the present invention, provides the 9-oxo-13-trans-prostenoic acid derivatives wherein Z is a divalent radical selected from the group consisting of $-(CH_2)_n-$, $-(CH_2)_n-O-CH_2-$, $-(CH_2)_n-S-CH_2-$,

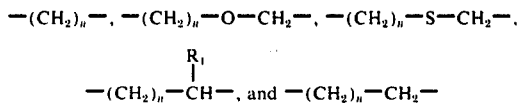

wherein $n$ and $R_1$ are as hereinbefore defined; $R'$ is a lower alkyl group, preferably methyl or n-butyl; and $R_2$ is a straight chain alkyl group having from 3 to 10 carbon atoms, a straight chain alkyl group having from 2 to 6 carbon atoms and having one branched methyl group, a straight chain alkenyl group having from 4 to 6 carbon atoms, or a straight chain ω-chloroalkyl group having from 3 to 6 carbon atoms. The compounds (XLIX) are readily prepared by the conjugate 1,4-addition of an alanate salt (XLVIII) to a 2 substituted cyclopent-2-en-1-one (XLVII). The yields of this operation are usually high and a clean product, uncontaminated with 1,2-addition product, is usually obtained. Furthermore, the transfer of the alkene group is effected with retention of the trans-configuration of the hydrogen atoms attached to the double bond, and no reaction is noted at the carbethoxy function of (XLVII). Another noteworthy aspect of this reaction is that it does not require a catalyst. The alanate salts (XLVIII) are conveniently prepared by the reaction of an appropriate 1-alkyne ($R_2$—C≡CH) with diisobutylaluminum hydride, followed by reaction with a lower alkyl lithium derivative, preferably methyl lithium or n-butyl lithium. Suitable 1-alkynes which may be thus employed are, for example, 1-pentyne, 1-hexyne, 1-decyne, 1-hendecyne, 1-dodecyne, 3-methyl-1-butyne, 1-heptyne, 1-oxtyne, 1-nonyne, 5-methyl-1-hexyne, 7-methyl-1-octyne, 7-methyl-1-nonyne, 3-methyl-1-octyne, 4-methyl-1-octyne, oct-5-en-1-yne, hept-5-en-1-yne, hex-4-en-1-yne, 5-chloro-1-pentyne, 6-chloro-1-hexyne, 7-chloro-1-heptyne, 8-chloro-1-octyne, etc. The reaction of the 1-alkyne with diisobutylaluminum hydride cleanly provides the trans-double bond and is preferably carried out in an inert solvent such as benzene, toluene, and the like at temperatures in the range of 40°–60° C. for several hours. The solvent is removed in vacuo and the subsequent reaction with methyl or n-butyl lithium is preferably carried out in an ether-type solvent such as diethyl ether, dibutyl ether, tetrahyrofuran, and the like. This reaction is rapid and is preferably carried out at 0°–10° C. with cooling. The conjugate 1,4-addition of the resulting alanate salt (XLVIII) to the cyclopent-2-en-1-one (XLVII) is preferably carried out at ambient temperatures for a period of 12 to 24 hours. This reaction is also best carried out in an ether-type solvent such as diethyl ether, dibutyl ether, tetrahydrofuran, and the like. The intermediate alanate-enolate adduct is then hydrolyzed in situ with dilute hydrochloric acid with cooling, and the products (XLIX) are isolated in the usual manner well known in the art. The conversion of the esters (XLIX) to the acids (L) is readily accomplished by mild saponification procedures such as in 0.5N aqueous-methanolic KOH at room temperature for 20–48 hours.

Other 9-oxo-13-trans-prostenoic acid derivatives maybe prepared as illustrated by the following flow-sheets wherein p is an integer from 2 to 4, inclusive; q is an integer from 3 to 6, inclusive; $R_3$ is a lower alkyl group having up to 3 carbon atoms; $R_4$ is hydrogen or lower alkyl; $R_5$ is hydrogen or lower alkyl; and $R_4$ and $R_5$ taken together with the N(nitrogen) is pyrrolidino, morpholino or piperidino.

FLOWSHEET G

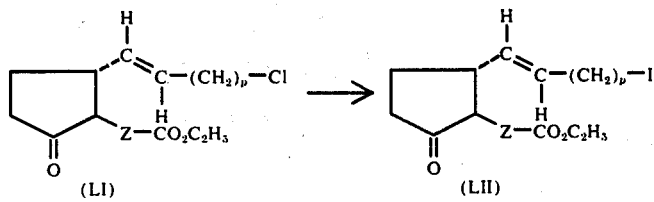

FLOWSHEET G-continued
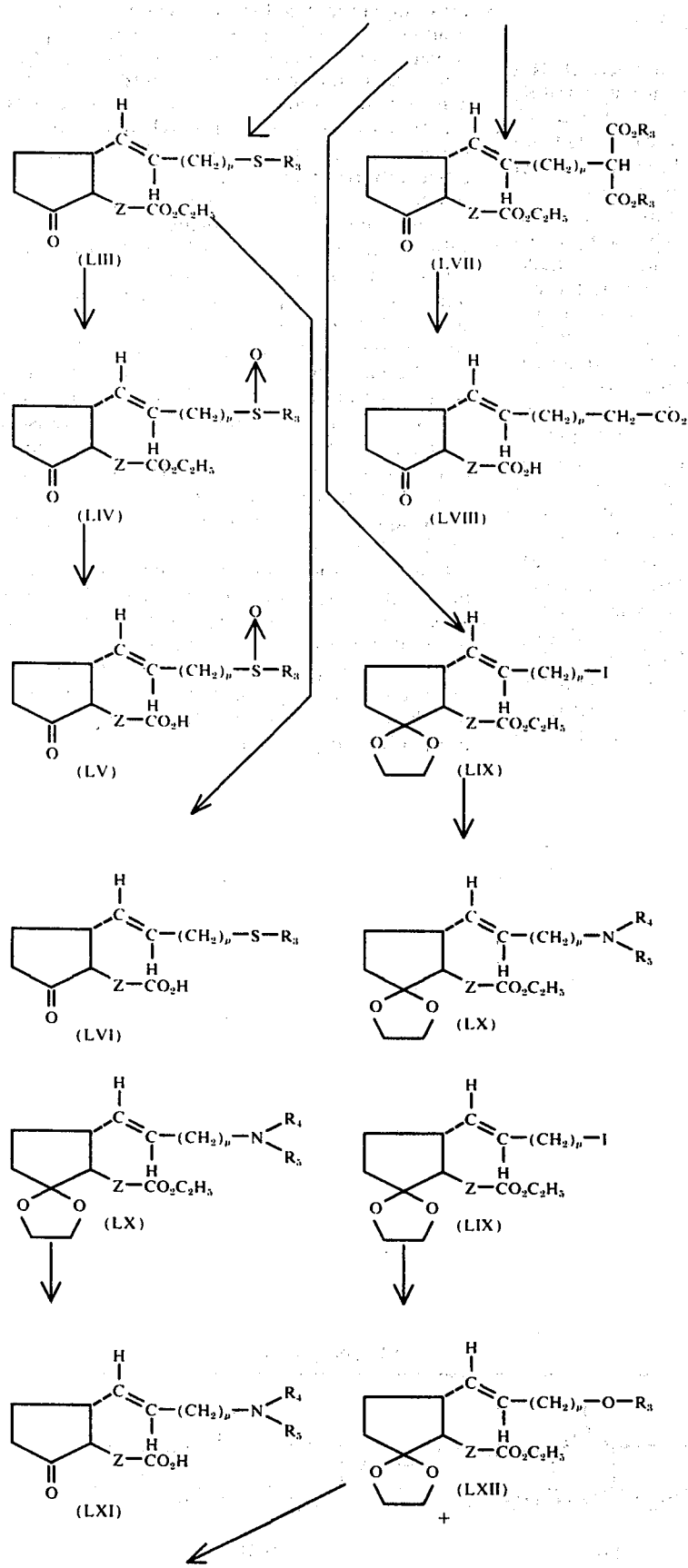

FLOWSHEET G-continued

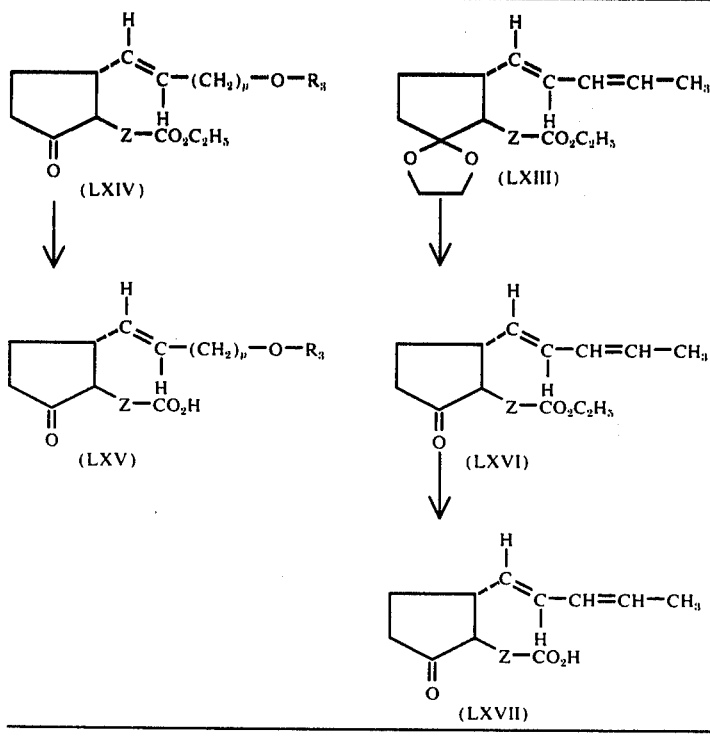

In Flowsheet G, treatment of the chloro derivative (LI) with sodium iodide provides the iodo derivative (LII), which on treatment with the sodium salt of an alkyl mercaptan furnishes the thia derivative (LIII), saponification of which give (LVI). Sulfur-oxidation of (LIII) with an equivalent of sodium metaperiodate affords the sulfoxide ester (LIV), which on saponification gives the corresponding acid (LV).

When the iodo derivative (LII) is treated with diethy sodio malonate the triester (LVII) results, which on saponification provides the corresponding triacid, heating of which in refluxing xylene causes decarboxylation of the substituted malonic acid to give the diacid (LVIII).

For some displacement reactions it is preferable to protect the ring ketone function in (LII). This can be accomplished by conversion to the ethylene ketal derivatives (LIX). Treatment of (LIX) with pyrrolidine gives the pyrrolidino derivative (LX), acid hydrolysis of the ketal blocking group then gives the keto-aminoacid (LXI). Treatment of iodo ketal (LIX) with a metal alkoxide provides a mixture of the oxa derivative (LXII) and the diene (LXIII), separable by chromatography. Ketal hydrolysis with acetone and p-toluenesulfonic acid of these two ketal esters gives the corresponding keto ester (LXIV) and (LXVI) respectively, saponification of which furnishes the keto acids (LXV) and (LXVII), respectively.

Additional transformations are illustrated in Flowsheet H, wherein q and Z are as hereinabove defined, R'' is hydrogen or lower alkyl, R''' is lower alkyl, and R'' and R''' taken together with the N(itrogen) is pyrrolidino, piperidino or morpholino.

FLOWSHEET H

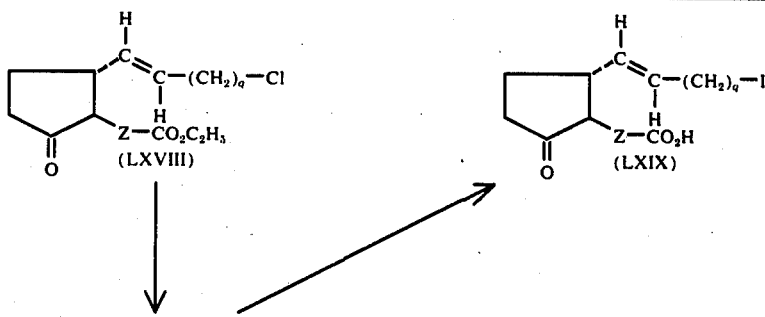

FLOWSHEET H-continued

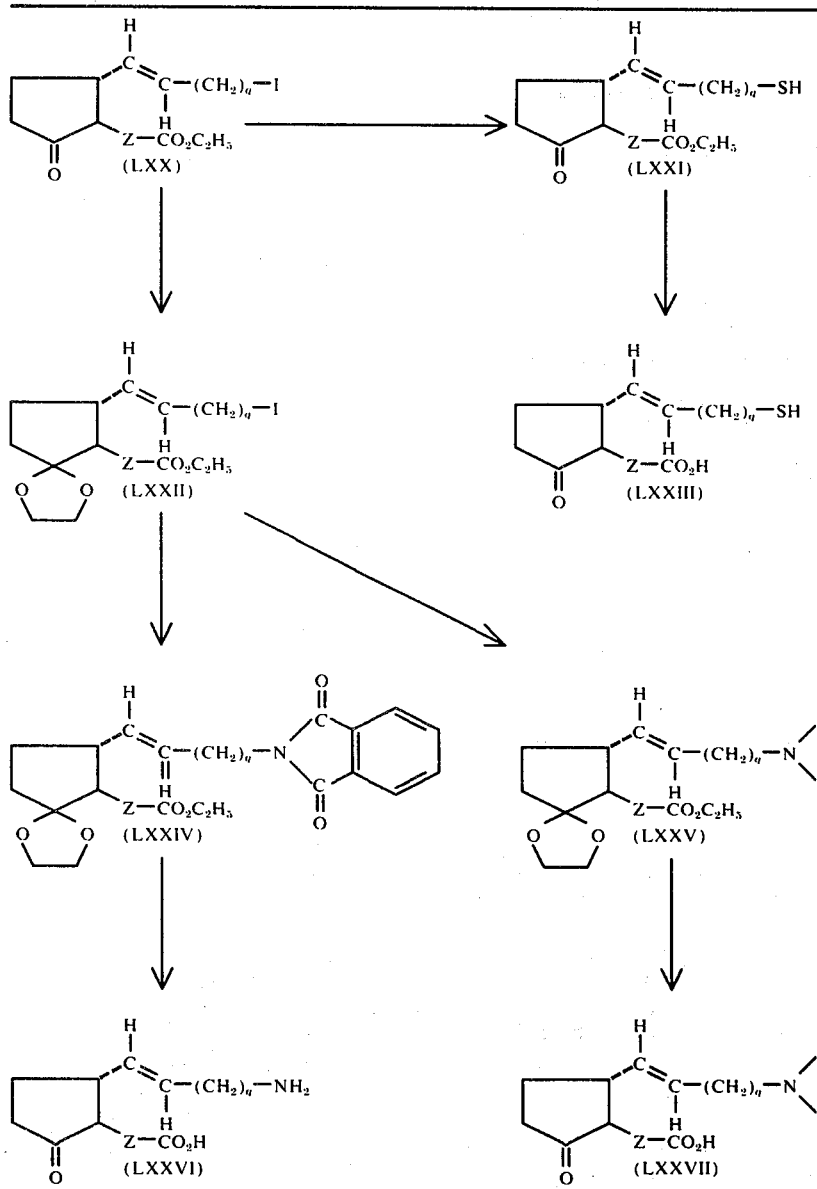

In accordance with Flowsheet H, treatment of the chloroketone (LXVIII) with sodium iodide in refluxing acetone produces the iodoketo ester (LXX), mild saponification of which provides the corresponding acid (LXIX). Treatment of the iodoketone ester with thiourea, followed by treatment of the intermediate thiuronium salt with an equivalent of alkali affords the mercapto ketoester (LXXI), which on saponification gives the corresponding acid (LXXII). Other transformations are preferably carried out after blocking the ring keto function as an ethylene ketal, thus the preparation of compound (LXXII). Reaction of ketal (LXXII) with potassium phthalimide in dimethylformamide (preferably at about 70° C. for about two hours) furnishes the phthalimido ketal (LXXIV). Deblocking of (LXXIV) to the amino ketoacid (LXXVI) is accomplished by first treating with potassium hydroxide in aqueous methanol followed by heating at reflux for about eighteen hours with aqueous hydrochloric acid. Substituted amino groups can be introduced by treating iodo ketal (LXXII) with various amines

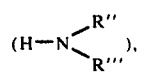

to give (LXXV) followed by ester and ketal hydrolysis to the amino ketoacids (LXXVII).

Additional transformations are illustrated in Flowsheet J, wherein p and $R_2$ are as defined hereinbefore. The synthesis of those compounds embodying at the same time Z as

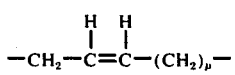

can be accomplished by transformations of (LXXX) or (LXXXI) wherein $R_2$ contains an $\omega$-chloroalkyl group in the manner described above in Flowsheets G and H.

In Flowsheet J, which follows, the ring carbonyl function of the 2-(carbethoxymethyl)cyclopentanone (LXXVIII) is blocked by conversion to the ketal (LXXIX). The ester function in (LXXIX) is then reduced to an aldehyde by treatment with diisobutylaluminum hydride. This reaction is preferably carried out by addition of one molecular equivalent of this reagent to a solution of ester (LXXIX) in hexane or other hydrocarbon solvent, cooled to −78° C. After about 2.5 hours at this temperature the entire reaction mixture is poured quickly into aqueous excess mineral acid, and the product aldehyde (LXXXI) is obtained upon immediate work-up in the usual way. The aldehyde (LXXXI) is then converted to (LXXX) by addition of (LXXXI) to the ylid prepared from (ω-carboxyalkyl)triphenyl phosphonium bromide and two molecular equivalents of sodium hydride in anhydrous dimethylsulfoxide. The use of dimethylsulfoxide as a solvent for this reaction leads to the predominant formation of the desired cis double bond in product (LXXX). The ketal blocking group in (LXXX) is then cleaved by treatment with acetone and p-toluenesulfonic acid producing the keto acid.

All of the prostaglandin-like compounds can be isolated and purified by conventional methods. Isolation can be accomplished, for example, by dilution of the reaction mixture with water, extraction with a water-immiscible solvent such as methylene chloride, ethyl acetate, benzene, cyclohexane, ether, toluene and the like, chromatography, adsorption on ion-exchange resins, distillation, or a combination of these. Purification of the compounds can be accomplished by means known in the art for the purification of prostaglandins and lipids, fatty acids, and fatty esters. For example, reverse phase partition chromatography, countercurrent distribution, adsorption chromatography on acid washed Florisil (synthetic magnesium silicate) and acid washed silica gel, preparative paper chromatography, preparative thin layer chromatography, chromatography over silver loaded cation exchange resins, and combinations thereof can be used effectively to purify the prostaglandin-like compounds.

The racemic prostaglandin-like compounds can be resolved into their optically active components by a

FLOWSHEET J

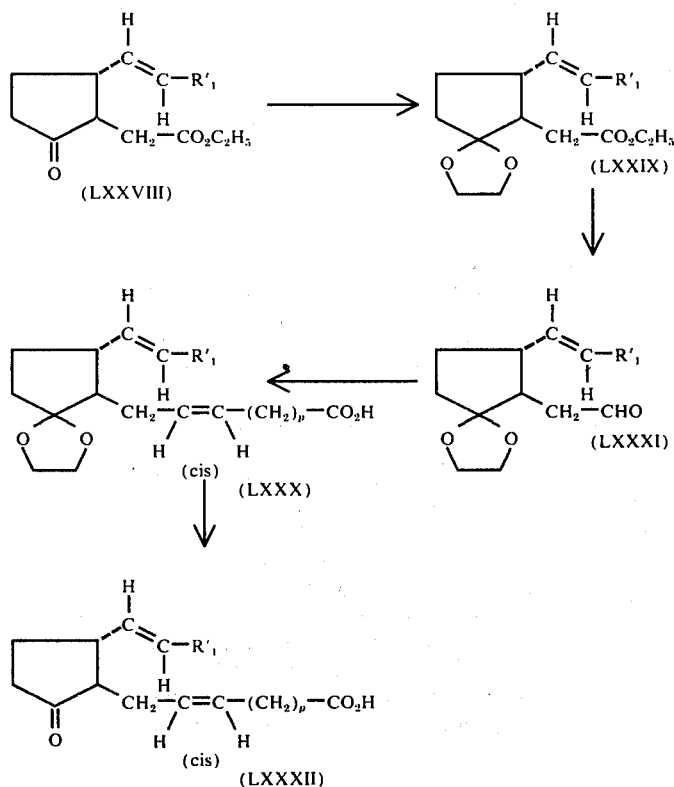

The various 9-hydroxy derivatives are prepared by reduction of the corresponding 9-keto ester or by subsequent transformations of the reduction product of the type recorded in Flowsheets G and H. Saponification of the ester provides the corresponding 9-hydroxy acids. The reduction is preferably carried out in the usual manner with sodium borohydride in ethanol as a solvent. The prostanoic acids are convertable to the corresponding ester by first treating with thionyl chloride and then reacting the resulting acid chloride with an appropriate alcohol in the presence of an acid acceptor, e.g., diethylamine. The new ester can then undergo the transformations illustrated in Flowsheets G and H.

number of methods of resolution well known in the art. For example, compounds L, LV, LVI, LVIII, LXI, LXV, LXVII, LXIX, LXXIII, LXXVI, LXXVII and LXXXII can all be obtained as free acids. These acids can be treated with an optically active base such as cinchonine, quinine, brucine, d- or 1-α-phenylethylamine and the like to produce diastereoisomeric salts which can be separated by crystallization. Alternatively, the acid may be esterified with an optically active alcohol, e.g., d- or l-menthol, estradiol 3-acetate, etc., and the diastereoisomeric esters then resolved.

Resolution of the racemic prostaglandin-like compounds can also be accomplished by reverse phase and absorption chromatography on an optically active support and adsorbent and by selective transformation of one isomer with a biologically active prostaglandin transforming system. Such transformations can be carried out by incubation or perfusion using methods well established in the art, followed by isolation and recovery of the isomer resistant to the metabolic transformation applied. The prostaglandin-like compounds are obtainable as yellow oils having characteristic absorption spectra. They are relatively soluble in common organic solvents such as ethanol, ethyl acetate, dimethylformamide, and the like.

The prostaglandin-like compounds are useful as hypotensive agents and their prostaglandin-like hypotensive activity was demonstrated in the following test procedure. This procedure is a modification of the technique described by Pike et al., *Prostaglandins, Nobel Symposium* 2, Stockholm, June, 1966; p. 165.

Male Wistar strain rats (Royal Hart Farms) averaging approximately 250 grams in weight were fastened to rat boards in a supine position by means of canvas vests and limb ties. The femoral area was infiltrated subcutaneously with lidocaine and the iliac artery and vein were exposed and cannulated. Arterial blood pressure (systolic/diastolic) was recorded using a Statham $P_{23}$ Db pressure transducer-Offner dynograph system. To obtain a stable blood pressure, the animals were anesthetized before use with pentobarbital, 30 mg./kg. of body weight intravenously, and also were given hexamethonium bitartrate, 2 mg./kg. of body weight intravenously. The test compounds were prepared by ultrasonic dispersion in a saline-Tween 80 vehicle. A constant intravenous dose volume of 0.5 ml. was administered and test doses ranged from 0.1 to 10.0 mg./kg. of body weight. Increasing or decreasing doses were selected depending on the dose response obtained. In Table I below are set forth the minimal doses required to produce a decrease of about 10 mm. in diastolic blood pressure for typical compounds.

TABLE I

| Compound | Minimal Effective Dose (mg./kg. of body weight) |
| --- | --- |
| ethyl 9-oxo-13-trans-prostenoate | 0.5 |
| ethyl 20-butyl-9-oxo-13-trans-prostenoate | 10 |
| ethyl 20-chloro-9-oxo-13-trans-prostenoate | 0.5 |
| ethyl 9-oxo-20-nor-13-trans-prostenoate | 0.6 |
| ethyl 20-methyl-9-oxo-13-trans-prostenoate | 0.5 |
| ethyl 17-methyl-9-oxo-19,20-dinor-13-trans-prostenoate | 10 |
| ethyl 20-chloro-9-oxo-17,18,19-trinor-13-trans-prostenoate | 0.2–1 |
| ethyl 9-oxo-13-trans-17-cis-prostadienoate | 0.2–2 |
| ethyl 9-oxo-3,4,5,6,7-pentanor-13-trans-prostenoate | 8 |
| ethyl 9-oxo-10a-homo-13-trans-prostenoate | 2 |
| ethyl 9-oxo-18-thia-13-trans-prostenoate | 2 |
| ethyl 9-oxo-18-oxythia-13-trans-prostenoate | 2 |
| ethyl 20,20-dicarbethoxy-9-oxo-18,19-dinor-13-trans-prostenoate | 8 |
| 9-oxo-13-trans-prostenoic acid | 0.4 |
| 9-oxo-6,7-dinor-13-trans-prostenoic acid | 2 |
| 20-chloro-9-oxo-13-trans-prostenoic acid | 0.5 |
| 9-oxo-20-nor-13-trans-prostenoic acid | 0.5–1 |
| 20-methyl-9-oxo-13-trans-prostenoic acid | 0.5–2 |
| 17-methyl-9-oxo-19,20-dinor-13-trans-prostenoic acid | 0.5 |
| 20-chloro-9-oxo-17,18,19-trinor-13-trans-prostenoic acid | 2–8 |
| 9-oxo-13-trans-17-cis-prostadienoic acid | 0.2 |
| 9-oxo-3,4,5,6,7-pentanor-13-trans-prostenoic acid | 2 |
| 9-oxo-10a-homo-13-trans-prostenoic acid | 0.2 |
| 9-oxo-18-thia-13-trans-prostenoic acid | 0.2 |
| 9-oxo-18-oxythia-13-trans-prostenoic acid | 2–8 |
| 20-chloro-9-hydroxy-17,18,19-trinor-13-trans-prostenoic acid | 2 |
| 17-methyl-9-hydroxy-19,20-dinor-13-trans-prostenoic acid | 0.2–2 |
| 9-hydroxy-6,7-dinor-13-trans-prostenoic acid | 2 |
| 20-carboxy-9-oxo-18,19-dinor-13-trans-prostenoic acid | 8 |
| 18-oxa-9-oxo-13-trans-prostenoic acid | 2 |
| 3-pyridyl 9-oxo-13-trans-prostenoate | 0.4–4 |
| n-butyl 9-oxo-13-trans-prostenoate | 2 |
| β-dimethylaminoethyl 9-oxo-13-trans-prostenoate | 0.5–2 |
| 9-hydroxy-13-trans-prostenoic acid | 2 |

This hypotensive effect is shortacting and a continuous infusion of compound is necessary to maintain the effect. Nevertheless, it is authoritatively claimed that hypotension induced by prostaglandins is of an ideal nature and therefore, despite the necessity of infusion, these compounds may be useful in the treatment of certain hypertensive crisis situations such as eclampsia. A description of this problem appears in The Medical Letter on Drugs and Therapeutics (p. 31–32, issue of April 3, 1970). Also, in a news item from *Medical World News*, 10, 12 (August 1, 1969), Dr. J. B. Lee, associate professor of medicine at St. Louis University, is quoted as saying that the related prostaglandin A compounds "might be useful in a hupertensive crisis such as eclampsia." The natural prostaglandins are only difficultly available, and at great cost. Thus, although the prostaglandin congeners and derivatives may be less potent and larger doses would probably be necessary, the greater availability of these compounds should provide a substantial economic advantage.

The prostaglandin-like compounds are also useful as antimicrobial agents. They possess antibacterial and antifungal activity in vitro against a variety of standard laboratory microorganisms as determined by the agar-dilution streak-plate technique. In this assay, the compounds to be tested are made up to contain 2.5 mg. of test compound per milliliter of solution. Observing sterile techniques, two-fold serial dilutions are made of each test solution. One milliliter of each of the original solutions and of each of the serial dilutions is then added to 9 ml. of warm sterile nutrient agar capable of supporting growth of the bacterial test cultures. A second set of agar dilutions is prepared identical to the first except that the nutrient agar is designed to support the growth of the fungal test cultures. The standard sterile nutrient agar solutions containing the different dilutions of the test compounds, along with suitable and comparable control dilutions containing no test compound, are then allowed to cool in Petri dishes thereby forming solidified agar plates. The test bacteria and yeast-like fungi are prepared for use by growing in broth overnight. The spores of the filamentous fungi are harvested from mature agar slant cultures and are suspended in sterile physiological saline solution. A loopful of each of the resulting live suspensions is then, still employing sterile techniques, streaked upon the surfaces of each of the agar plates and the resulting streaked plates are then incubated. After an appropriate period of time, each of the streaks on each of the plates is inspected visually and the extent, if any, of bacterial or fungal growth is noted. The minimal inhibitory concentration (expressed in micrograms per milliliter) is defined as the concentration of test compound causing complete inhibition of growth of any particular organism.

In a representative operation, and merely by way of illustration, the minimal inhibitory concentration of typical compounds against a variety of test organisms as determined in the above-described assay are set forth in Tables II and III below:

TABLE II

| Compound | Minimal inhibitory conc. (mcg./ml.) | | | |
|---|---|---|---|---|
| | (1) | (2) | (3) | (4) |
| 9-oxo-13-trans-prostenoic acid | 50 | 50 | 50 | 50 |
| 9-oxo-18,19,20-trinor-13-trans-prostenoic acid | | 250 | 250 | 250 |
| ethyl 9-oxo-18,19,20-trinor-13-trans-prostenoate | | | | 250 |
| ethyl 15-methyl-9-oxo-17,18,19-20-tetranor-13-trans-prostenoate | 250 | 250 | 250 | 250 |
| 20-butyl-9-oxo-13-trans-prostenoic acid | | | 250 | |
| ethyl 20-butyl-9-oxo-13-trans-prostenoate | | | 250 | |
| 20-chloro-9-oxo-13-trans-prostenoic acid | 250 | 62 | 16 | 62 |
| ethyl 20-chloro-9-oxo-13-trans-prostenoate | | | 250 | 250 |
| 9-oxo-20-nor-13-trans-prostenoic acid | 50 | 50 | 25 | 25 |
| 20-methyl-9-oxo-13-trans-prostenoic acid | 100 | 50 | 25 | 25 |
| 17-methyl-9-oxo-19,20-dinor-13-trans-prostenoic acid | 50 | 50 | 25 | 25 |
| 9-oxo-10a-homo-13-trans-prostenoic acid | | | 100 | 100 |
| ethyl 20-chloro-9-oxo-17,18,19-trinor-13-trans-prostenoate | | | | 250 |
| 20-chloro-9-oxo-17,18,19-trinor-13-trans-prostenoic acid | 250 | 250 | 250 | 250 |
| 9-oxo-6,7-dinor-13-trans-prostenoic acid | 250 | 250 | 250 | 250 |
| 9-hydroxy-13-trans-prostenoic acid | 50 | 25 | 50 | 50 |
| β-dimethylaminoethyl 9-oxo-13-trans-prostenoate | 250 | | 250 | |
| ethyl 20-iodo-9-oxo-17,18,19-trinor-13-trans-prostenoate | | | 250 | 250 |
| 9-oxo-18-thia-13-trans-prostenoic acid | | 250 | 125 | 125 |
| ethyl 9-oxo-18-oxythia-13-trans-prostenoate | | | 250 | 250 |
| 9-hydroxy-6,7-dinor-13-trans-prostenoic acid | 250 | 62 | 62 | 62 |
| 18-oxa-9-oxo-13-trans-prostenoic acid | | | 250 | 250 |
| 9-oxo-13-trans-17-cis-prostadienoic acid | 125 | 62 | 62 | 62 |
| 20-chloro-9-hydroxy-17,18,19-trinor-13-trans-prostenoic acid | | 250 | 250 | 250 |
| 17-methyl-9-hydroxy-19,20-dinor-13-trans-prostenoic acid | | 62 | 62 | 62 |
| ethyl 9-oxo-3,4,5,6,7-pentanor-13-trans-prostenoate | | | 250 | 125 |
| 20-mercapto-9-oxo-13-trans-prostenoic acid | | 125 | 250 | 250 |
| 9-oxo-3,4,5,6,7-pentanor-13-trans-prostenoic acid | 250 | 250 | 125 | 250 |

(1) Microsporum canis ATCC 10214
(2) Microsporum gypseum ATCC 14683
(3) Trichophyton tonsurans NIH 662
(4) Trichophyton mentagrophytes E 11

TABLE III

| Compound | Minimal inhibitory conc. (mcg./ml.) | | | |
|---|---|---|---|---|
| | (5) | (6) | (7) | (8) |
| 9-oxo-13-trans-prostenoic acid | 250 | 62 | 250 | 62 |
| 9-oxo-18,19,20-trinor-13-trans-prostenoic acid | | | | 250 |
| ethyl 9-oxo-18,19,20-trinor-13-trans-prostenoate | | 250 | | |
| ethyl 15-methyl-9-oxo-17,18,19-20-tetranor-13-trans-prostenoate | 250 | 62 | | |
| 20-butyl-9-oxo-13-trans-prostenoic acid | | 10 | | 10 |
| ethyl 20-butyl-9-oxo-13-trans-prostenoate | | 250 | | |
| 20-chloro-9-oxo-13-trans-prostenoic acid | 62 | 250 | 250 | 62 |
| ethyl 20-chloro-9-oxo-13-trans-prostenoate | 250 | 250 | | |
| ethyl 9-oxo-20-nor-13-trans-prostenoate | | 62 | | |
| 9-oxo-20-nor-13-trans-prostenoic acid | 50 | 62 | 250 | 62 |
| 20-methyl-9-oxo-13-trans-prostenoic acid | 100 | 25 | 50 | 10 |
| ethyl 17-methyl-9-oxo-19,20-dinor-13-trans-prostenoate | | 62 | | |
| 17-methyl-9-oxo-19,20-dinor-13-trans-prostenoic acid | 50 | 62 | 250 | 62 |
| 9-oxo-10a-homo-13-trans-prostenoic acid | | 25 | 100 | 10 |
| ethyl 20-chloro-9-oxo-17,18-19-trinor-13-trans-prostenoate | | 250 | | |
| 20-chloro-9-oxo-17,18,19-trinor-13-trans-prostenoic acid | 250 | | | |
| 3-pyridyl 9-oxo-13-trans-prostenoate | | 50 | | |
| ethyl 9-oxo-18-thia-13-trans-prostenoate | | 250 | | |
| n-butyl 9-oxo-13-trans-prostenoate | | 250 | | 250 |
| ethyl 9-oxo-6,7-dinor-13-trans-prostenoate | | 250 | | |
| 9-oxo-6,7-dinor-13-trans-prostenoic acid | 250 | 250 | 250 | 250 |
| 9-hydroxy-13-trans-prostenoic acid | | 25 | 50 | 25 |
| β-dimethylaminoethyl 9-oxo-13-trans-prostenoate | | 10 | 50 | 10 |
| ethyl 9-hydroxy-13-trans-prostenoate | | 25 | | |
| ethyl 20-iodo-9-oxo-17,18,19-trinor-13-trans-prostenoate | | 62 | | |
| ethyl 20-iodo-9-oxo-13-trans-prostenoate | | 62 | | |
| 9-oxo-18-thia-13-trans-prostenoic acid | | 250 | | |
| ethyl 20,20-dicarbethoxy-9-oxo-18,19-dinor-13-trans-prostenoate | | 250 | | |
| ethyl 9-oxo-18-oxythia-13-trans-prostenoate | 250 | 250 | | |
| ethyl 9-hydroxy-6,7-dinor-13-trans-prostenoate | | 6 | | 13 |
| 9-hydroxy-6,7-dinor-13-trans-prostenoic acid | 250 | 62 | 250 | 62 |
| 9-oxo-13-trans-17-cis-prostadienoic acid | 125 | 62 | 250 | 62 |
| 20-chloro-9-hydroxy-17,18,19-trinor-13-trans-prostenoic acid | | | | 62 |
| 17-methyl-9-hydroxy-19,20-dinor-13-trans-prostenoic acid | 250 | 62 | 125 | 25 |
| ethyl 9-oxo-3,4,5,6,7-pentanor-13-trans-prostenoate | | 125 | | 125 |
| 20-mercapto-9-oxo-13-trans-prostenoic acid | | 125 | | 6 |
| 9-oxo-3,4,5,6,7-pentanor-13-trans-prostenoic acid | 250 | | | |

(5) Trichophyton rubrum E 97
(6) Mycobacterium smegmatis ATCC 606
(7) Staphylococcus aureus Rose ATCC 14154
(8) Streptococcus pyogenes C 203

All of the compounds of this invention can be isolated and purified by conventional methods. Isolation can be accomplished, for example, by dilution of the reaction mixture with water, extraction with a water-immiscible solvent such as methylene chloride, ethyl acetate, benzene, cyclohexane, ether, toluene and the like, chromatography, adsorption on ion-exchange resins, distillation, or a combination of these. Purification of the compounds of this invention can be accomplished by means known in the art.

The novel compounds of the present invention are obtainable as yellow oils as solids having characteristic absorption spectra. They are relatively soluble in common organic solvents such as ethanol, ethyl acetate dimethylformamide, and the like.

The invention will be described in greater detail in conjunction with the following specific examples.

EXAMPLE 1

Preparation of 2-carbalkoxy(methyl/ethyl)-2-(4-carbethoxybutyl)-cyclopentan-1-one To a stirred solution of the sodium cyclopentanone carboxylate enolate in dimethoxyethane, prepared from 187 g. (1.248 moles) of 2-cyclopentanone carboxylate (mixed methyl and ethyl esters), 52.4 g. (1.248 moles) sodium hydride (57.2% in mineral oil) and 1.6 l. of dimethoxyethane, is added dropwise 309 g. (1.212 moles) of ethyl 5-iodovalerate. The reaction mixture is stirred and heated at reflux for 18 hours. The mixture is cooled and filtered. The solvent is removed from the filtrate by evaporation and the residue is poured into dilute hydrochloric acid and extracted with ether. The combined extracts are washed with water and saline, dried over magnesium sulfate and evaporated to give an oil. The oil is distilled under reduced pressure to give 274 g. of a light yellow oil, b.p. 140°–143° C. (0.17 mm).

EXAMPLE 2

Preparation of 2-(4-carboxybutyl)cyclopentan-1-one

A stirred mixture of 274 g. of 2-carbalkoxy(mixed methyl and ethyl esters)-2-(4-carbethoxybutyl)cyclopentan-1-one (Example 1), 600 ml. of 20% hydrochloric acid and 325 ml. of acetic acid is heated at reflux for 20 hours. Solution occurs in approximately ½ hour. The solution is cooled and diluted with water and extracted with ether. The combined extracts are washed with saline and dried over magnesium sulfate and evaporated. The residue is evaporated twice with toluene to give 144 g. of an oil.

EXAMPLE 3

Preparation of 2-(4-carbethoxybutyl)cyclopentan-1-one

A stirred solution of 124 g. (0.673 mole) of 2-(4-carboxybutyl)cyclopentan-1-one (Example 2), 800 ml. of ethanol and 1 g. of p-toluenesulfonic acid monohydrate is heated at reflux for 18 hours. The solvent is evaporated and the residue is dissolved in ether. The ether solution is washed with saline, dilute sodium bicarbonate solution and again with saline, dried over magnesium sulfate and evaporated. The oil is distilled under reduced pressure to give 149 g. of a colorless oil, b.p. 106°–109° C. (0.23 mm).

EXAMPLE 4

Preparation of 2-carbalkoxy(methyl/ethyl)-2-(3-carbethoxypropyl-cyclopentan-1-one In the manner described in Example 1, treatment of 2-cyclopentanone carboxylate (mixed methyl and ethyl esters) with sodium hydride in dimethoxyethane followed by ethyl 4-iodobutyrate gives a yellow oil, b.p. 136°–137° C. (0.16 mm).

EXAMPLE 5

Preparation of 2-(3-carboxypropyl)cyclopentan-1-one

In the manner described in Example 2, treatment of 2-carbalkoxy(mixed methyl and ethyl esters)-2-(3-carbethoxypropyl)cyclopentan-1-one (Example 4) with a 20% hydrochloric acid and acetic acid mixture gives a yellow oil.

EXAMPLE 6

Preparation of 2-(3-carbethoxypropyl)cyclopentan-1-one

In the manner described in Example 3, treatment of 2-(3-carboxypropyl)cyclopentan-1-one (Example 5) with p-toluenesulfonic acid monohydrate in ethanol gives a colorless oil, b.p. 93° C. (0.10 mm).

EXAMPLE 7

Preparation of ethyl and methyl 2-(6-carbethoxyhexyl)-1-cyclopentanon-2-carboxylate In the manner described in Example 1, ethyl and methyl 2-cyclopentanone carboxylate is reacted with ethyl 7-bromoheptanoate to furnish the subject product, b.p. 147° C. (0.09 mm).

EXAMPLE 8

Preparation of 2-(6-carboxyhexyl)cyclopentan-1-one

In the manner described in Example 2, ethyl and methyl 2-(6-carbethoxyhexyl)-1-cyclopentanone-2-carboxylate (Example 7) is hydrolyzed to furnish the subject product, b.p. 143° C. (0.05 mm).

EXAMPLE 9

Preparation of 2-(6-carbethoxyhexyl)cyclopentan-1-one

In the manner described in Example 3, 2-(6-carboxyhexyl)cyclopentan-1-one (Example 8) is esterified to furnish the subject product, b.p. 110° C. (0.03 mm).

EXAMPLE 10

Preparation of 1-acetoxy-2-(6-carbethoxyhexyl)cyclopent-1-ene

A stirred solution of 100 g. of 2-(6-carbethoxyhexyl)-cyclopentan-1-one Example 9) in 250 ml. of acetic anhydride containing 0.940 g. of p-toluenesulfonic acid monohydrate is heated to boiling under partial reflux allowing distillate at 118° C. or less (i.e., acetic acid) to escape through a Vigreux column equipped with a condenser to collect the distillate. After 16 hours, during which period acetic anhydride is added in portions in order to keep the solvent level at at least 100 ml., the solution is cooled and poured cautiously into a stirred cold mixture of saturated sodium bicarbonate solution (400 ml.) and nexane (250 ml.). The resulting mixture is stirred for an additional 30 minutes during which period solid sodium bicarbonate is added periodically to insure a basic solution. The hexane layer is separated and washed with saturated sodium chloride solution, dried with anhydrous magnesium sulfate and taken to dryness. Distillation of the residual oil gives 102 g. (87%) of pale yellow oil, b.p. 118° C. (0.07 mm.).

EXAMPLE 11

Preparation of
1-acetoxy-2-(3-carboxythoxypropyl)cyclopent-1-ene

In the manner described in Example 10, treatment of 2-(3-carbethoxypropyl)cyclopentan-1-one (Example 6) with acetic anhydride and p-toluenesulfonic acid monohydrate gives a yellow oil, b.p. 98°–103° C, (0.35 mm).

EXAMPLE 12

Preparation of
1-acetoxy-2-(4-carbethoxybutyl)cyclopent-1-ene

In the manner described in Example 10, treatment of 2-(4-carbethoxybutyl)cyclopentan-1-one (Example 3) with acetic anhydride and p-toluenesulfonic acid monohydrate gives a yellow oil, b.p. 109°–110° C. (0.37 mm).

EXAMPLE 13

Preparation of
2-(6-carbethoxyhexyl)cyclopent-2-en-1-one

To a rapidly stirred mixture of 50 g. of 1-acetoxy-2-(6-carbethoxyhexyl)cyclopent-1-ene (Example 10) in 150 ml. of chloroform, 200 ml. of water and 18.8 g. of calcium carbonate, cooled in an ice bath, is added dropwise over a period of about 30 minutes, a solution of 30 g. of bromine in 50 ml. of carbon tetrachloride. After stirring for an additional 45 minutes the chloroform layer is separated and washed successively with dilute sodium thiosulfate solution, saturated sodium chloride solution, dried with anhydrous magnesium sulfate and taken to dryness under reduced pressure.

The residual oil is dissolved in 50 ml. of N,N-dimethylformamide and added to a mixture of 33 g. of lithium bromide and 32 g. of lithium carbonate in 375 ml. of N,N-dimethylformamide, previously dried by refluxing with 375 ml. of benzene under a Dean-Stark apparatus followed by distillation of the benzene. The mixture is stirred at the reflux temperature for 30 minutes, then cooled and poured into 850 ml. of ice-cold water. The resulting mixture is acidified (cautiously) with 4N hydrochloric acid and extracted with ether three times. The combined ether extracts are washed with saturated sodium chloride solution, dried with anhydrous magnesium sulfate and taken to dryness under reduced pressure to afford 41.5 g. of an amber oil. In order to convert any isomeric material to the desired product, 41.5 g. of the above material is treated with 0.500 g. of p-toluenesulfonic acid monohydrate in 450 ml. of absolute alcohol at the reflux temperature for 18 hours. The solution is taken to dryness under reduced pressure. The resulting gum is dissolved in ether and washed with saturated sodium bicarbonate solution, saturated sodium chloride solution, dried with anhydrous magnesium sulfate and taken to dryness under pressure. The residual oil is distilled to give 30.2 g. of produce; b.p. 118° C. (0.05 mm.); $\lambda_{max}^{MeOH}$ 229 mµ ($\epsilon$9950); $\lambda_{max}$ 5.75, 5.85, 6.15, 8.45 µ; phase chromatography shows 99% product, containing 1% 2-(6-carbethyoxyhexyl)-cyclopentan-1-one.

This product can be purified by the following procedure. A mixture of 120 g. of 2-(6-carbethoxyhexyl)-2-cyclopentenone, containing approximately 5% of the saturated analogue, and 7.67 g. (10 mole percent) of p-carboxyphenylhydrazine in 400 ml. of absolute ethanol is stirred at ambient temperatures for 18 hours and is then refluxed for 1 hour. The mixture is cooled, the solvent is evaporated, and the residue is taken up into 150 ml. of chloroform and passed through a column of 450 g. of aluminum oxide (Merck). The filtrate is evaporated to yield a colorless oil containing < 0.5% of the saturated impurity.

EXAMPLE 14

Preparation of
2-(3-carbethoxypropyl)cyclopent-2-en-1-one

In the manner described in Example 13, bromination of 1-acetoxy-2-(3-carbethoxypropyl)cyclopent-1-ene (Example 11) followed by dehydrobromination with lithium bromide and lithium cabonate is productive of the subject compound.

EXAMPLE 15

Preparation of
2-(4-carbethoxybutyl)cyclopent-2-en-1-one

In the manner described in Example 13, treatment of 1-acetoxy-2-(4-carbethoxybutyl)cyclopent-1-ene (Example 12) with bromine and subsequent treatment of the brominated product with a mixture of lithium bromide and lithium carbonate in N,N-dimethylformamide is productive of the subject compound. Treatment of this product with p-carboxyphenylhydrazine by the procedure of Example 13 furnishes a product which contains less than 0.5% of the corresponding saturated ketone.

EXAMPLE 16

Preparation of
1-methoximino-2-(6-carbethoxyhexyl)-2-cyclopentene

To a mixture of 35.97 g. (0.151 mole) of 2-(6-carbethoxyhexyl)-2-cyclopentenone (Example 13) and 15.0 g. (0.180 mole) of methoxyamine hydrochloride in 300 ml. of absolute ethanol is added 25 ml. of pyridine and the resulting solution is stirred for 20 hours at ambient temperatures. The solvent is evaporated and the residue is partitioned between water and diethyl ether. The organic phase is washed with water and saturated brine, dried ($Na_2SO_4$), and the solvent is evaporated to yield an oil. Distillation yields 38.7 g. of a colorless oil, b.p. 115°–118° C. (0.075 mm). IR (film): 1740, 1627, 1053, 890 $cm^{-1}$. $\lambda_{max}$ (MeOH) 243 (13,000). NMR δ ($CDCl_3$): 3.89.

EXAMPLE 17

Preparation of
1-methoximino-2-(7-hydroxyheptyl)-2-cyclopentene

To an ice cooled solution of 34.10 g. (0.128 mole) of 1-methoximino-2-(6-carbethoxyhexyl)-2-cyclopentene (Example 16) in 200 ml. of benzene under nitrogen is added dropwise 225 ml. of a 25% solution of diisobutyl aluminium hydride in hexane. The resulting solution is stirred for 2 hours at 0°–5° C., poured onto ice and dilute hydrochloric acid, and the aqueous phase is saturated with sodium chloride. The organic phase is separated, washed with saturated brine, dried ($Na_2SO_4$), and evaporated to yield an oil. The latter is dissolved in 100 ml. of hot hexane and cooled to yield 24.3 g. of crystals, m.p. 62°–64° C. IR (KBr) 3260, 1630, 1059, 893 $cm^{-1}$ $\lambda_{max}$ 243 (14,200). NMR ($CDCl_3$) δ; 2.37.

EXAMPLE 18

Preparation of 1-methoximino-2-(7-p-toluenesulfonyloxyheptyl)-2-cyclopentene

To a solution of 5.00 g. (0.0222 mole) of 1-methoximino-2-(7-hydroxyheptyl)-2-cyclopentene (Example 17) in 50 ml. of dry pyridine at 0° C. is added 8.45 g. (0.0444 mole) of p-toluenesulfonyl chloride and the resulting solution is chilled at 5° C. overnight. The mixture is partitioned between 300 ml. of ice water and diethyl ether. The organic phase is washed with 1:1 ice cold hydrochloric acid, cold water, and cold saturated brine, dried ($NaSO_4/K_2CO_3$), and evaporated under reduced pressure at room temperature to yield an oil. The latter is dissolved in 600 ml. of hexane, treated with 0.5 g. of Darco, filtered and evaporated to yield 7.7 g. of a colorless oil. IR (film) 1600, 1192, 1182, 1053, 890 $cm^{-1}$. $\lambda_{max}$ (MeOH) 228 and 243.

EXAMPLE 19

Preparation of 1-methoximino-2-(8,8-dicarbethoxyoctyl)-2-cyclopentene

To an alcoholic solution of diethyl sodio malonate, prepared from 0.847 g. (0.0368 g. atoms) of sodium, 100 ml. of absolute ethanol, and 7.05 g. (0.0440 mole) of diethyl malonate is added 7.7 g. of the tosylate of Example 18 and the mixture is refluxed for 2 hours under a nitrogen atmosphere. The mixture is partitioned between cold dilute hydrochloric acid and diethyl ether, and the organic phase is washed with water and saturated brine, dried ($Na_2SO_4$), and evaporated to yield an oil. The excess diethyl malonate is distilled off under reduced pressure to yield 6.45 g. of a yellowish oil. IR (film) 1755, 1728, 1625, 1054, 890 $cm^{-1}$.

EXAMPLE 20

Preparation of 1-methoximino-2-(8,8-dicarboxyoctyl)-2-cyclopentene

A mixture of 6.45 g. of the diester of Example 19 and 6.72 g. of potassium hydroxide in 150 ml. of 1:1 aqueous methanol is refluxed for 1 hour, cooled, and is partitioned between water and diethyl ether. The aqueous phase is acidified with hydrochloric acid, extracted with ether, and the organic phase is washed with water and saturated brine, dried ($Na_2SO_4$) and evaporated to yield a solid. The solid is crystallized from benzene to yield 4.15 g. of tan crystals, m.p. 135°–137° C. ($-CO_2$).

EXAMPLE 21

Preparation of 1-methoximino-2-(8-carboxyoctyl)-2-cyclopentene

A solution of 3.926 g. (0.0126 mole) of the diacid of Example 20 in 20 ml. of xylene is refluxed for 1.5 hours, cooled, and evaporated to yield a tan solid. IR (KBr) 1720, 1618, 1179, 1050, 986 $cm^{-1}$.

EXAMPLE 22

Preparation of 2-(8-carboxyoctyl)cyclopent-2-en-1-one

The acid methoxime from Example 21 is refluxed for 5 hours with 55 ml. of acetone and 20 ml. of 2N hydrochloric acid. The mixture is cooled, the solvent is evaporated, and the residue is partitioned between water and diethyl ether. The organic phase is washed with water and saturated brine, dried ($Na_2SO_4$), and evaporated to yield a tan solid. IR (KBr) 1745, 1665 $cm^{-1}$. $\lambda_{max}$ (MeOH) 228 (12,600).

EXAMPLE 23

Preparation of 2-(8-carbethoxyoctyl)cyclopent-2-en-1-one

The acid ketone from Example 22 is Fisher esterified with 100 ml. of absolute ethanol, 100 ml. of benzene, and 20 mg. of p-toluenesulfonic acid for 6 hours, cooled, and the solvent is evaporated. The resulting oil is dissolved in 3:1 benzene-ether and the solution is passed through a column of 100 g. of Florisil. The filtrate is evaporated and the residue is distilled to yield 2.97 g. of a colorless oil, b.p. 137°–139° C. (0.05 Torr).

EXAMPLE 24

Preparation of 2-(4-carbethoxybutyl)-2-cyclopentenone methoxime

Treatment of 2-(4-carbethoxybutyl)-2-cyclopentenone (Example 15) with methoxyamine hydrochloride in the manner described in Example 16 gives an oil, b.p. 107°–109° C. (0.05 mm). IR (film): 1740, 1628, 1050, 885 $cm^{-1}$. $\lambda_{max}$ (MeOH) 243 ((13,600).

EXAMPLE 25

Preparation of 2-(5-hydroxypentyl)-2-cyclopentenone methoxime

Treatment of 2-(4-carbethoxybutyl)-2-cyclopentenone as methoxime (Example 24) with diisobutyl aluminum hydride in the manner described in Example 17 gives crystals, m.p. 33°–35° C. IR (KBr) 3420, 1630, 1050, 886 $cm^{-1}$ $\lambda_{max}^{MeOH}$ 243 (12,020).

EXAMPLE 26

Preparation of 2-(5-p-toluenesulfonyloxypentyl)-2-cyclopentenone methoxime

Treatment of 2-(hydroxypentyl)-2-cyclopentenone methoxime (Example 25) with p-toluenesulfonyl chloride in pyridine in the manner described in Example 18 gives a colorless oil. IR (film) 1600, 1190, 1180, 1050, 885 $cm^{-1}$.

EXAMPLE 27

Preparation of 2-(6,6-dicarbethoxyoctyl)-2-cyclopentenone methoxime

To a solution of diethyl sodio ethylmalonate, prepared from 1.63 g. (0.0387 mole) of sodium hydride in mineral oil (57.2%) and 8.5 g. (0.0452 mole) of diethyl ethylmalonate in 100 ml. of ethylene glycol dimethyl ether, is added 7.5 g. of tosylate from Example 26 in 20 ml. of ethylene glycol dimethyl ether and the mixture is refluxed for 3 hours and then allowed to stand at room temperature for 18 hours under nitrogen atmosphere. The reaction mixture is filtered and most of the solvent is removed. The mixture is partitioned between cold dilute hydrochloric acid and diethyl ether, and the organic phase is washed with water and saturated brine, dried ($MgSO_4$), and evaporated to yield an oil. The excess diethyl ethylmalonate is distilled off under reduced pressure to yield 6.7 g. of a yellow oil. IR (film) 1755, 1728, 1627, 1050, 885 $cm^{-1}$.

EXAMPLE 28

Preparation of 2-(6,6-dicarboxyoctyl)-2-cyclopentenone methoxime

Treatment of 2-(6,6-dicarbethoxyoctyl)-2-cyclopentenone methoxime (Example 27) with potassium hydroxide, and 1:1 aqueous methanol in the manner described in Example 20 gives a light yellow oil.

EXAMPLE 29

Preparation of 2-(6-carboxyoctyl)-2-cyclopentenone methoxime

In the manner described in Example 21, treatment of 2-(6,6-dicarboxyoctyl)-2-cyclopentenone methoxime (Example 28) with xylene at reflux for 18 hours gives a yellow oil.

EXAMPLE 30

Preparation of 2-(6-carboxyoctyl)-2-cyclopentenone

Treatment of 2-(6-carboxyoctyl)-2-cyclopentenone methoxime (Example 29) with acetone and 2N hydrochloric acid in the manner described in Example 22 gives a light yellow oil.

EXAMPLE 31

Preparation of 2-(6-carbethoxyoctyl)-2-cyclopentenone

Treatment of 2-(6-carboxyoctyl)-2-cyclopentenone (Example 30) with thionyl chloride and then treatment of the acid chloride with ethanol gives an amber oil. The oil is placed on a magnesia-silica gel column and eluted with 3:1 benzene:ether. The solvent is removed and the residue is distilled, b.p. 122° C. (0.06 mm).

EXAMPLE 32

Preparation of 2-(3-carbethoxypropyl)-1-methoximino-2-cyclopentene

In the manner described for the preparation of the compound of Example 16, 2-(3-carbethoxypropyl)-1-methoximino-2-cyclopentene is prepared from 2-(3-carbethoxypropyl)-2-cyclopentenone (Example 14) and methoxyamine hydrochloride.

EXAMPLE 33

Preparation of 2-(4-hydroxybutyl)-1-methoximino-2-cyclopentene

In the manner described for the preparation of the compound of Example 17, 2-(4-hydroxybutyl)-1-methoximino-2-cyclopentene is prepared from 2-(3-carbethoxypropyl)-1-methoximino-2-cyclopentene and diisobutylaluminum hydride.

EXAMPLE 34

Preparation of 2-(6-carbethoxy-5-oxahexyl)-1-methoximino-2-cyclopetene

To an ice cold solution of 4.833 g. (0.0266 mole) of 2-(4-hydroxybutyl)-1-methoximino-2-cyclopentene in 50 ml of dry tetrahydrofuran under nitrogen is added 16.7 ml. of 1.6 molar n-butyl lithium in hexane, dropwise. The reaction mixture is stirred for 0.5 hour and then 4.85 g. (0.029 mole) of ethyl bromoacetate is added dropwise. The reaction mixture is stirred overnight at room temperature and then refluxed for 1.5 hours. The reaction is cooled and poured into water and extracted several times with ether. The ether extracts are washed with saline, dried over magnesium sulfate, and concentrated. The residue is placed on an alumina column, chloroform being used as a wash solvent. The combined washings are concentrated to dryness to give 4.903 g. of product as a yellow oil.

EXAMPLE 35

Preparation of 2-(6-carboxy-5-oxahexyl)-2-cyclopentenone

In the manner described in Example 22, treatment of 2-(6-carbethoxy-5-oxahexyl)-1-methoximino-2-cyclopentene with acetone and 2N hydrochloric acid at reflux gives the subject compound as a yellow oil.

EXAMPLE 36

Preparation of 2-(6-carbethoxy-5-oxahexyl)-2-cyclopentenone

In the manner described in Example 23, treatment of 2-(6-carboxy-5-oxahexyl)-2-cyclopentenone with p-toluenesulfonic acid in ethanol produces the subject product as a light yellow oil

EXAMPLE 37

Preparation of 2-(4-toluenesulfonyloxybutyl)-1-methoximino-2-cyclopentene

In the manner described in Example 18, treatment of 2-(4-hydroxybutyl)-1-methoximino-2-cyclopentene with p-toluene sulfonyl chloride in pyridine gives the subject product as a light yellow oil; IR (film): 1600, 1190, 1050, 885 cm$^{-1}$.

EXAMPLE 38

Preparation of 2-(6-carbethoxy-5-thiahexyl)-1-methoximino-2-cyclopentene

To a stirred mixture of 1.465 g. (0.0348 mole) of sodium hydride (57.2% in mineral oil) in 50 ml. of dimethoxyethane, under nitrogen, is added slowly 4.8 g. (0.0347 mole) of ethyl 2-mercaptoacetate. The reaction mixture is stirred at room temperature for one hour and then a solution of 7.8 g. (0.0231 mole) of 2-(4-p-toluenesulfonyloxybutyl)-1-methoximino-2-cyclopentene in 30 ml. of dimethoxyethane is added dropwise and stirred at room temperature for 18 hours. The solution is heated at reflux for one hour, cooled and poured into cold dilute hydrochloric acid and then extracted with ether. The combined ether extracts are washed with saline, dried over magnesium sulfate and evaporated to give 7.6 g. of subject product as a yellow oil

EXAMPLE 39

Preparation of 2-(6-carboxy-5-thiahexyl)-2-cyclopentenone

In the manner described in Example 22, treatment of 2-(6-carbethoxy-5-thiahexyl)-1-methoximino-2-cyclopentene with acetone and 2N hydrochloric acid at reflux gives the subject product as a yellow oil.

EXAMPLE 40

Preparation of
2(6-carbethoxy-5-thiahexyl)-2-cyclopentenone

In the manner described in Example 23, treatment of 2-(6-carboxy-5-thiahexyl)-2-cyclopopententenone with p-toluenesulfonic acid in ethanol gives the subject ester as a yellow oil.

EXAMPLE 41

Preparation of
2-(6-carboxy-5-oxahexyl)-1-methoximino-2-cyclopentene

To an ice cold solution of 3.66 g. (0.02 mole) of 2-(4-hydroxybutyl)-1-methoximino-2-cyclopentene (Example 33) in 50 ml. of 1,2-dimethoxyethane under nitrogen is added dropwise 17 ml. of 1.6 M n-butyl lithium in hexane. The reaction mixture is stirred for half an hour and then the lithium salt of chloroacetic acid, prepared from 1.89 g. (0.02 mole) of chloroacetic acid and 16 ml. of 1.6 M n-butyl lithium in 20 ml. of dimethoxyethane, is added and the reaction mixture is heated at reflux for 48 hours. The solvent is evaporated and the residue is partitioned between ether and water. The aqueous phase is acidified with hydrochloric acid and extracted with ether. The organic phase is washed with water and saturated saline solution, dried ($MgSO_4$), and evaporated to give 3.35 g. of a yellow oil.

EXAMPLE 42

Preparation of
2-(6-carboxy-5-oxahexyl)-2-cyclopenten-1-one

In the manner described in (Example 22), treatment of 2-(6-carboxy-5-oxahexyl)-1-methodximino-2-cyclopentene (Example 41) with acetone and 2N hydrochloric acid at reflux gives the subject compound as a yellow oil.

EXAMPLE 43

Preparation of
1-methoximino-2-(4-methanesulfonyloxybutyl)-2-cyclopentene

To a solution of 1.83 g. (0.01 mole) of 1-methoximino-2-(4-hydroxybutyl)-2-cyclopentene (Example 33) in 10 ml. of methylene chloride containing 1.52 g. (0.015 mole) of triethylamine is added 1.265 g. (0.011 mole) of methanesulfonyl chloride over a period of 5–10 minutes at −10–0° C. Stirring is continued for 15 minutes and the solution is then washed with cold water, cold 10% hydrochloric acid, cold sodium bicarbonate solution, and cold saline solution. The organic phase is dried ($MgSO_4$) and concentrated to give an oil which solidifies upon cooling. Crystallization from ether-petroleum ether (30°–60° C.) gives 1.797 g. of white crystals, m.p. 67°–68° C.

EXAMOLE 44

Preparation of
1-methoximino-2-(5-cyanopentyl)-2-cyclopentene

A mixture of 2.75 g. (0.01 mole) of 1-methoximino-2-(5-methanesulfonyloxypentyl)-2-cyclopentene (Example 54) and 1.47 g. (0.03 mole) of sodium cyanide in 20 ml. of dry N,N-dimethylformamide is heated at 65°–70° C. for 3 hours. The cooled reaction mixture is poured into water and extracted with diethyl ether. The organic phase is washed with water and saturated saline solution, dried ($MgSO_4$), and evaporated to give 1.89 g. of a light yellow oil.

EXAMPLE 45

Preparation of
1-methoximino-2-(5-carboxypentyl)-2-cyclopentene

A mixture of 1.89 g. (0.0092 mole) of 1-methoximino-2-(5-cyanopentyl)-2-cyclopentene (Example 44) and 1 g. (0.025 mole) of sodium hydroxide in 50 ml. of 1:1 aqueous-ethanol is refluxed for 48 hours, cooled, and partitioned between water and diethyl ether. The aqueous phase is acidified with hydrochloric acid, extracted with diethyl ether, and the organic phase is washed with water and saturated saline solution, dried ($MgSO_4$), and evaporated to give 1.86 g. of a yellow oil.

EXAMPLE 46

Preparation of 2-(5-carboxypentyl)-2-cyclopentenone

A solution of 1.86 g. (0.00825 mole) 1-methoximino-2-(5-carboxypentyl)-2-cyclopentene (Example 45) in 44 ml. of acetone and 13.1 ml. of 2N hydrochloric acid is refluxed for 5 hours. The solvent is partially evaporated and a solid precipitates and is collected. The residue is extracted with diethyl ether and the organic phase is washed with saturated saline solution, dried ($MgSO_4$), and evaporated to yield additional solid. The combined solid material is crystallized from ether/pet ether (30°–60° C.) to yield crystalline material, m.p. 70°–72° C.

EXAMPLE 47

Preparation of
2-(5-carbethoxypentyl)-2-cyclopentenone

A solution of 1.309 g. (0.00668 mole) of 2-(5-carboxypentyl)-2-cyclopentenone (Example 46) and 90 mg. of p-toluenesulfonic acid in 150 ml. of ethanol is refluxed for 18 hours. The solvent is evaporated and the residue is dissolved in ether. The organic phase is washed with water, sodium bicarbonate solution, and saturated saline solution, dried ($MgSO_4$), and evaporated to give 1.371 g. of a light yellow oil.

EXAMPLE 48

Preparation of
2-(5-acetoxypentyl)-2-carbomethoxy/carbethoxy-cyclopentanone

A mixture of sodiocyclopentanone carboxylate, prepared from 1200 g. (8.0 moles) of cyclopentanone carboxylate (methyl and ethyl esters) and 200 g. (8.3 moles) of mineral oil free sodium hydride in 10 l. of 1,2-dimethoxyethane, 1320 g. (8.0 moles) of 5-chloro-1-amyl acetate [M. E. Synerholm, *Journ. Amer. Chem. Soc.*, 69, 2681 (1947)], and 1200 g. (8.0 moles) of sodium iodide is refluxed under nitrogen for 18 hours. The mixture is cooled, concentrated to 4 l., and partitioned between dilute hydrochloric acid and diethyl ether. The organic phase is washed with water and saturated brine, dried ($MgSO_4$), and evaporated to yield 1920 g. of an oil.

EXAMPLE 49

Preparation of
2-(5-hydroxypentyl)cyclopentanone/2-(5-acetoxypentyl)-cyclopentanone A mixture of 4,500 g. (16.2 moles) of 2-(5-acetoxypentyl)-2-carbomethoxy/carbomethoxy-cyclopentanone (Example 48), 2.2 l. of glacial acetic acid, 1 l. of concentrated hydrochloric acid, and 1 l. of water is refluxed for 18 hours, cooled, and partitioned between saturated brine and benzene. The organic phase is washed with saturated brine, dried (MgSO$_4$), and evaporated in vacuo to yield 3155 g. of an oil.

EXAMPLE 50

Preparation of
1-acetoxy-2-(5-acetoxypentyl)-1-cyclopentene

A solution of 400 g. (2.04 moles) of a mixture of 2-(5-hydroxypentyl)cyclopentanone and 2-(5-acetoxypentyl(cyclopentanone (Example 49) and 4.0 g. of p-toluenesulfonic acid monohydrate in 1 l. of acetic anhydride is refluxed at a rate to maintain a steady distillation of acetic acid from the reaction through a helice-packed fractionation column. The reaction is continued with the addition of acetic anhydride to maintain a constant volume until complete conversion of starting materials to product is evident. The mixture is cooled and partitioned between 2 l. of hexane and 3 l. of cold water containing solid sodium bicarbonate to maintain a neutral pH. The organic phase is washed with saturated brine, dried (MgSO$_4$), and evaporated to yield 452 g. of an oil.

EXAMPLE 51

Preparation of 2-(5-acetoxypentyl)-2-cyclopentenone

To a well stirred mixture of 405 g. (4.05 moles) of calcium carbonate, 3 l. of water, and 2.5 l. of chloroform cooled to 5° C. is added simultaneously 1016 g. (4.0 moles) of 1-acetoxy-2-(5-acetoxy-pentyl)-1-cyclopentene (Example 50) and a solution of 648 g. (4.08 moles) of bromine in 500 ml. of carbon tetrachloride at a rate to maintain a temperature below 10° c. The mixture is stirred for half an hour after addition of the reagents and the phases are then separated. The organic phase is washed with 2% sodium thiosulfate solution, water, and saturated brine, dried (MgSO$_4$), and evaporated in vacuo to an oil. The oil is immediately added to a refluxing slurry of 500 g. (5.0 moles) of calcium carbonate in 2.5 l. of N,N-dimethylacetamide under nitrogen and the mixture is then refluxed for thirty minutes. The mixture is cooled, filtered and partitioned between water and diethyl ether. The organic phase is washed with water and saturated brine, dried (MgSO$_4$), and evaporated to yield 757 g. of an oil, b.p. 116°-118° C. (0.25 mm.).

EXAMPLE 52

Preparation of
1-methoximino-2-(5-acetoxypentyl)-2-cyclopentene

In the manner described for Example 16. 2-(5-acetoxypentyl)-2-cyclopentenone (Example 51) is treated with methoxyamine hydrochloride in pyridine and ethanol to yield the subject compound, b.p. 101°-103° C. (0.20 mm.).

EXAMPLE 53

Preparation of
1-methoximino-2-(5-hydroxypentyl)-2-cyclopentene

A mixture of 74 g. (0.22 mole) of 1-methoximino-2-(5-acetoxypentyl)-2-cyclopentene (Example 52) and 56 g. (1.0 mole) of potassium hydroxide in 300 ml. of 1:1 aqueous methanol is refluxed for 2 hours and then cooled. The solvent is partially removed in vacuo and the residue is partitioned between saturated brine and diethyl ether. The organic phase is washed with saturated brine, dried (MgSO$_4$), and evaporated to yield an oil which crystallized, m.p. 35°-36° C.

EXAMPLE 54

Preparation of
1-methoximino-2-(5-methanesulfonyloxypentyl)-2-cyclopentene

To a cold solution of 9.85 g. (0.05 mole) of 1-methoximino-2-(5-cyclopentene (Example 53) and 7.6 g. (0.075 mole) of triethylamine in 100 ml. of methylene chloride at a rate to maintain a temperature of −10° to 0° C. The mixture is then stirred for 15 minutes and then poured into ice water. The organic phase is washed with cold 10% hydrochloric acid, cold saturated sodium bicarbonate solution, and cold saturated brine, dried (MgSO$_4$), and evaporated to yield a solid, m.p. 78°-80° C.

EXAMPLE 55

Preparation of
1-methoximino-2-(6,6-dicarbethoxyhexyl)-2-cyclopentene

To a suspension of sodiodiethylmalonate in 1,2-dimethoxyethane, prepared from 248 g. (1.55 moles) of diethyl malonate and 17.2 g. (0.95 mole) of mineral oil free sodium hydride in 1 l. of 1,2-dimethoxyethane under nitrogen, is added 170 g. (0.62 mole) of 1-methoximino-2-(5-methanesulfonyloxypentyl)-2-cyclopentene (Example 54 ) in 1.5 l. of 1,2-dimethoxyethane and the mixture is refluxed for 5 hours. The mixture is cooled, filtered, and the solvent is evaporated. Theresidue is partitioned between cold dilute hydrochloric acid and water, and the organic phase is washed with saturated brine, dried (MgSO$_4$), evaporated to remove solvent and excess diethyl malonate to yield 209 g. of an oil.

EXAMPLE 56

Preparation of
1-methoximino-2-(6,6-dicarboxyhexyl)-2-cyclopentene

In the manner described in Example 20, 1-methoximino-2-(6,6-dicarbethoxyhexyl)-2-cyclopentene is treated with potassium hydroxide in 1:1 aqueous methanol and then hydrochloric acid to yield the desired compound as crystals from diethyl ether, m.p. 110°-115° C.

EXAMPLE 57

Preparation of
1-methoximino-2-(6-carboxhexyl)-2-cyclopentene

A solution of 141 g. (0.50 mole) of 1-methoximino-2-(6,6-dicarboxyhexyl)-2-cyclopentene in 500 ml. of bis-(2-methoxyethyl) ether is refluxed for 2 hours, cooled, and evaporated to yield an oil. The latter is

EXAMPLE 58

Preparation of 2-(6-carboxyhexyl)-2-cyclopentenone

In the manner described in Example 22, treatment of 1-methoximino-2-(6-carboxyhexyl)2-cyclopentene (Example 57) with acetone and 2N hydrochloric acid at reflux provides the subject compound.

EXAMPLE 59

Preparation of 2-(6-carbethoxyhexyl)-2-cyclopentenone

Fischer esterification of 2-(6-carboxyhexyl)-2-cyclopentenone (Example 58) in the manner of Example 23 provides the subject compound.

EXAMPLE 60

Preparation of 1-methoximino-2-(6-fluoro-6-dicarbethoxyhexyl)-2-cyclopentene

To a solution of sodiodiethyl fluoromalonate, prepared from 2.062 g. (0.0491 mole) of sodium hydride in mineral oil (57.2%), 40 ml. of dry N,N-dimethylformanide and 8.174 g. (0.0458 mole) of diethyl fluoromalonate is added dropwise 11.32 g (0.0413 mole) of 1-methoximino-2-(5-methylsulfonyloxypentyl)-2-cyclopentene (Example 54) in 60 ml. of N,N-dimethylformanide. The mixture is refluxed for 2 hours under a nitrogen atmosphere. The mixture is concentrated and partitioned between cold dilute hydrochloric acid and diethyl ether, and the organic phase is washed with saturated brine, dried ($MgSO_4$), and evaporated to yield 13.631 g. (92%) of a yellow oil.

EXAMPLE 61

Preparation of 1-methoximino-2-(6-fluoro,6-dicarboxyhexyl)-2-cyclopentene

A mixture of 13.631 g. of the diester of Example 60 and 16 g. of potassium hydroxide in 364 ml. of 1:1 aqueous methanol is refluxed for 5 hours, cooled, concentrated, and is partitioned between water and diethyl ether. The aqueous phase is acidified with hydrochloric acid, extracted with ether, and the organic phase is washed with saturated brine, dried ($MgSO_4$) and evaporated to yield a solid. The solid is crystallized from diethyl ether petroleum ether (30°–60° C.) to give 10 g. (90%) of white crystals, m.p. 143°–145° C. (—$CO_2$)

EXAMPLE 62

Preparation of 1-methoximino-2-(6-fluoro-6-carboxhexlyl)-2-cyclopentene

A solution of 10 g. of the diacid of Example 61 in 60 ml. of 2-methoxyethyl ether is refluxed for 7 hours, cooled, and evaporated to yield 8.5 g. (95%) of a tan solid. A sample is crystallized from diethyl ether-petroleum ether (30°–60° C.) to give white crystals, m.p. 98°–100° C.

EXAMPLE 63

Preparation of 2-(6-fluoro-6-carboxyhexyl)cyclopent-2-en-1-one

The acid methoxime (8.5 g.) from Example 62 is refluxed for 5 hours with 180 ml. of acetone and 64 ml. of 2N hydrochloric acid. The mixture is cooled, the solvent is evaporated, and the residue is partitioned between water and diethyl ether. The organic phase is washed with saturated brine, dried ($MgSO_4$) and evaporated to yield 7.4 g. (98%) of a light yellow oil.

EXAMPLE 64

Preparation of 2-(6-fluoro-6-carbethoxyhexyl)cyclopent-2-en-1-one

The acid ketone (7.4 g.) from Example 63 is Fischer esterified with 300 ml. of absolute ethanol and 400 mg. of p-toluenesulfonic acid for 18 hours, cooled, and the solvent is evaporated. The resulting oil is dissolved in ether, washed with dilute sodium bicarbonate solution, saline, dried ($MgSO_4$) and to give 7.306 g. (86%) of a light yellow oil.

EXAMPLE 65

Preparation of 2-(7-cyanoheptyl)-1-methoximino-2-cyclopentene

Treatment of 1-methoximino-2-(7-p-toluenesulfonyloxy)-2-cyclopentene (Example 18) with sodium cyanide in the manner of Example 44 is productive of the subject compound.

EXAMPLE 66

Preparation of 2-(7-carboxyheptyl)-1-methoximino-2-cyclopentene

Alkaline hydrolysis of 2-(7-cyanoheptyl)-1-methoximino-2-cyclopentene (Example 65) by the procedure of Example 45 is productive of the subject compound.

EXAMPLE 67

Preparation of 2-(7-carboxyheptyl)-2-cyclopenten-1-one

Hydrolysis of the methoxime of Example 66 with acetone-hydrochloric acid by the procedure of Example 46 is productive of the subject compound.

EXAMPLE 68

Preparation of 2-(7-carbethoxyheptyl)-2-cyclopenten-1-one

Fischer esterification of the carboxylic acid of Example 67 by the procedure of Example 47 is productive of the subject compound.

EXAMPLE 69

Preparation of 2-(6,6-dicarbethoxy-6-phenylhexyl)-1-methoximino-2-cyclopentene

Treatment of 1-methoximino-2-(5-methanesulfonyloxypentyl)-2-cyclopentene (Example 54) with sodio diethyl phenylmalonate by the procedure of Example 55 is productive of the subject compound.

EXAMPLE 70

Preparation of 2-(6,6-dicarboxy-6-phenylhexyl)-1-methoximino-2-cyclopentene

Alkaline hydrolysis of 2-(6,6-dicarbethoxy-6-phenylhexyl)-1-methoximino-2-cyclopentene (Example 69) by the procedure of Example 20 is productive of the subject diacid.

EXAMPLE 71

Preparation of 2-(6-carboxy-6-phenylhexyl)-1-methoximino-2-cyclopentene

Decarboxylation of 2-(6,6-dicarboxy-6-phenylhexyl)-1-methoximino-2-cyclopentene (Example 70) by the procedure of Example 57 is productive of the subject compound.

EXAMPLE 72

Preparation of 2-(6-carboxy-6-phenylhexyl)-2-cyclopentene-1-one

Methoxime cleavage of 2-(6-carboxy-6-phenylhexyl)-1-methoximino-2-cyclopentene (Example 71) in the manner of Example 63 is productive of the subject ketone.

EXAMPLE 73

Preparation of 2-(6-carbethoxy-6-phenylhexyl)-2-cyclopenten-1-one

Fischer esterification of the carboxylic acid of Example 72 in the manner of Example 64 is productive of the subject keto-ester.

EXAMPLE 74

Preparation of 2-(6-fluoro-6,6-dicarbethoxyhexyl)-1-methoximino-2-cyclopentene

An ethanolic solution of sodium ethoxide, prepared from 0.389 g. of sodium and 40 ml. of absolute ethanol, is treated at ambient temperatures with 5.05 g. of 2-(6,6-dicarbethoxyhexyl)-1-methoximino-2-cyclopentene (Example 55). The resulting solution is cooled to $-20°$ C. and then treated with a stream of perchloryl fluoride until the mixture becomes neutral. The excess perchloryl fluoride is removed with a stream of nitrogen and the mixture is retreated with 10 ml. of an ethanolic solution of sodium ethoxide (from 0.350 g. of sodium) and then with perchloryl fluoride until the mixture becomes neutral. The excess perchloryl fluoride is removed with a stream of nitrogen and the mixture is filtered and evaporated to an oil. The latter is partitioned between ether and water and the organic phase is washed with saturated saline, dried ($Na_2SO_4$) and evaporated to afford the subject compound.

EXAMPLE 75

Preparation of 2-(4-bromobutyl)-1-methoximino-2-cyclopentene

A mixture of 15.24 g. of 2-(4-p-toluenesulfonyloxybutyl)-1-methoximino-2-cyclopentene (Example 37) and 10.70 g. of sodium bromide in 100 ml. of dimethylsulfoxide is stirred at ambient temperature for 48 hours and then poured into 600 ml. of water. The mixture is extracted with hexane and its organic phase is wasted with saturated brine, dried ($NaSO_4$), and evaporated to yield a tan oil.

EXAMPLE 76

Preparation of 2-(4-iodobutyl)-1-methoximino-2-cyclopentene

To a solution of 1.5 g. of sodium iodide in 20 ml. of acetone is added 2.3 g. of 2-(4-bromobutyl)-1-methoximino-2-cyclopentene (Example 75) and the resulting mixture is stirred at ambient temperatures for 5 hours. The mixture is filtered and evaporated and the residue is partitioned between water and benzene. The organic phase is washed with saturated brine, dried ($NaSO_4$), and evaporated to yield a tan oil.

EXAMPLE 77

Preparation of 1-methoximino-2-(5-chloropentyl)-2-cyclopentene

A solution of 5 g. (0.0182 mole) of 2-(5-methylsulfonyloxypentyl)-2-cyclopentenone methoxime (Example 54) and 5 g. of lithium chloride in 100 ml. of N,N-dimethylformamide is heated at reflux for 1 hour. The solution is cooled and 100 ml. of water is added and extracted with diethyl ether. The combined extracts are washed with saline, dried ($MgSO_4$), and evaporated to yield a light yellow oil.

EXAMPLE 78

Preparation of 1-methoximino-2-(6,6-dicarbethoxyhexyl)cyclopent-2-ene

Treatment of 1-methoximino-2-(5-chloropentyl)-2-cyclopentene (Example 77) with sodio diethylmalonate in the manner of Example 55 is productive of the subject compound.

EXAMPLE 79

Preparation of 1-methoximino-2-(5,5-dicarbethoxypentyl)-2-cyclopentene

Treatment of 2-(4-iodobutyl)-1-methoximino-2-cyclopentene (Example 76) or of 2-(4-bromobutyl)-1-methoximino-2-cyclopentene (Example 75) with sodio diethylmalonate in the manner of Example 55 is productive of the subject compound.

EXAMPLE 80

Preparation of ethyl 9-oxo-13-trans-prostenoate

A solution of 1.102 g. of 1-octyne in 2 ml. of benzene is treated with 11.5 ml. of 15% diisobutylaluminum hydride in toluene and the solution is heated to 50° C. for 2 hours. The solution is cooled, its solvent is removed in vacuo, and the resulting oil is treated with 5.45 ml. of 5.10% methyl lithium in diethyl ester with ice cooling. To the resulting solution is added 1.830 g. of 2-(6-carbethoxyhexyl)-2-cyclopentenone (Example 13) and the solution is stirred at ambient temperatures for 18 hours. The solution is poured onto ice and dilute hydrochloric acid, and the mixture is extracted with diethyl ether. The organic phase is washed with dilute sodium bicarbonate, water, and saturated brine, dried and evaporated. The residue is purified by chromatography on Florisil and distillation to yield 1.878 g. of an oil, II 1736 $cm^{-1}$ (ester and ketone carbonyls) 969 $cm^{-1}$ (trans vinyl group); NMR ($CDCl_3$) δ5.14–5.87

(multiplet, 2H, vinyl protons, J trans=15 Hz); Mass Spectrum, parent peak at 350 mµ.

EXAMPLE 81

Preparation of ethyl 20-butyl-9-oxo-13-trans-prostenoate

In the manner described in Example 80, 2-(6-carbethoxyhexyl)-2-cyclopentenone (Example 13) is added to the reagent prepared from 1-dodecyne, diisobutylaluminum hydride, and methyl lithium. The crude product obtained by acid hydrolysis and ether extraction is purified by silica gel chromatography to give an oil, IR 1740 cm$^{-1}$ (ester and ketone carbonyls) 967 cm$^{-1}$ (trans vinyl group)

EXAMPLE 82

Preparation of ethyl 9-oxo-18,19,20-trinor-13-trans-prostenoate

In the manner described in Example 80, 2-(6-carbethoxyhexyl)-2-cyclopentenone (Example 13) is added to the reagent prepared from 1-pentyne, diisobutylaluminum hydride, and methyl lithium. The crude product obtained by acid hydrolysis and ether extraction is purified by distillation to give a liquid, IR 1740 cm$^{-1}$ (ester and ketone carbonyls) 967 cm$^{-1}$ (trans vinyl group).

EXAMPLE 83

Preparation of ethyl 15-methyl-9-oxo-17,18,19,20-tetranor-13-trans-prostenoate

In the manner described in Example 80, 2-(6-carbethoxyhexyl)-2-cyclopentenone (Example 13) is added to the reagent prepared from 3-methyl-1-butyne, diisobutylaluminum hydride, and methyl lithium. The crude product obtained by acid hydrolysis and ether extraction is purified by distillation to give a liquid, IR 1740 cm$^{-1}$ (ester and ketone carbonyls) 967 cm$^{-1}$ (trans vinyl group).

EXAMPLE 84

Preparation of ethyl 20-chloro-9-oxo-13-trans-prostenoate

In the manner described in Example 80, 2-(6-carbethoxyhexyl)-2-cyclopentenone (Example 13) is added to the reagent prepared from 8-chloro-1-octyne [W. J. Gensler and G. R. Thomas, J. Amer. Chem. Soc., 73, 4601 (1951)], diisobutylaluminum hydride, and methyl lithium. The crude product obtained by acid hydrolysis is purified by silica gel chromatography to give an oil, IR 1740 cm$^{-1}$ (ester and ketone carbonyls), 967 cm$^{-1}$ (trans vinyl group).

EXAMPLE 85

Preparation of ethyl 9-oxo-20-nor-13-trans-prostenoate

A solution of 5.30 g. of 1-heptyne in 10 ml. of benzene is treated with 40 ml. of 1.2N diisobutylaluminum hydride in hexane and heated at 50° C. for 2 hours. The solution is cooled in an ice bath and diluted with 25 ml. of ether. To the solution is added 30 ml. of 1.6M n-butyl lithium in hexane. After stirring for 20 minutes at 15°–25° C. the resulting solution is treated with a solution of 2-(6-carbethoxyhexyl)-2-cyclopentenone (Example 13). The mixture is stirred at 5°–25° C. for 18–20 hours and the product then is hydrolyzed with a mixture of ice and hydrochloric acid. The crude product, obtained from the organic phase, is purified by chromatography on silica gel to give an oil, IR 1740 cm$^{-1}$ (ester and ketone carbonyls) and 967 cm$^{-1}$ (trans vinyl group).

EXAMPLE 86

Preparation of ethyl 20-methyl-9-oxo-13-trans-prostenoate

In the manner described in Example 85, 2-(6-carbethoxyhexyl)-2-cyclopentenone (Example 13) is added to the reagent prepared from 1-nonyne, diisobutyl aluminum hydride and n-butyl lithium. The crude product obtained by acid hydrolysis and evaporation of organic solvent is purified by chromatography on silica gel to give an oil, IR 1740 cm$^{-1}$ (ester and ketone carbonyls) and 967 cm$^{-1}$ (trans vinyl group).

EXAMPLE 87

Preparation of ethyl 17-methyl-9-oxo-19,20-dinor-13-trans-prostenoate

In the manner described in Example 85, 2-(6-carbethoxyhexyl)-2-cyclopentenone (Example 13) is added to the reagent prepared from 5-methyl-1-hexyne, diisobutylaluminum hydride and n-butyl lithium. The crude product obtained by acid hydrolysis and evaporation of the organic solvent is purified by chromatography on silica gel to give an oil, IR 1740 cm$^{-1}$ (ester and ketone carbonyl) and 967 cm$^{-1}$ (trans vinyl group).

EXAMPLE 88

Preparation of ethyl 20-chloro-9-oxo-17,18,19-trinor-13-trans-prostenoate

In the manner described in Example 85, 2-(6-carbethoxyhexyl)-2-cyclopentenone (Example 13) is added to the reagent prepared from 5-chloro-1-pentyne, diisobutylaluminum hydride, and n-butyl lithium. The crude product, obtained by acid hydrolysis and evaporation of the organic solvent, is purified by distillation to give an oil, IR 1740 cm$^{-1}$ (ester and ketone carbonyls) and 967 cm$^{-1}$ (trans vinyl group).

EXAMPLE 89

Preparation of ethyl 9-oxo-13-propyl-18,19,20-trinor-13-trans-prostenoate

In the manner described in Example 85, 2-(6-carbethoxyhexyl)-2-cyclopentenone (Example 13) is added to the reagent prepared from 4-octyne, diisobutylaluminum hydride, and n-butyl lithium. The crude product mixture, obtained by acid hydrolysis and evaporation of the organic solvent, is separated by chromatography on silica gel and distillation to give ethyl 9-oxo-13-propyl-18,19,20-trinor-13-trans-prostenoate as an oil, IR 1740 cm$^{-1}$ (ester and ketone carbonyls); NMR (CCl$_4$) δ5.2 ppm (multiplet, vinyl proton) and a second oil (ethyl 9-oxo-17,18,19,20-tetranorprostanoate), IR 1740 cm$^{-1}$ (ester and ketone carbonyls), NMR (CCl$_4$) δ1.0 ppm (multiplet, terminal methyl group).

EXAMPLE 90

Preparation of cis-5-octen-1-yne

A 57% sodium hydride dispersion (9.66 g., 0.23 mole) is washed free of mineral oil in a nitrogen atmosphere with hexane. The hydride is heated at 75° C.

with 220 ml. of dimethyl sulfoxide for 45 minutes. The resulting green solution is cooled to 18° C. and treated with a solution of 4-pentynyl-triphenylphosphonium iodide (100 g., 0.22 mole) in 220 ml. of dimethylsulfoxide over a 25 minute period. The resulting red soluton is stirred at ambient temperature for 45 minutes. To the solution is added a solution of freshly distilled propionaldehyde (14.0 g., 0.24 mole) in 10 ml. of dimethylsulfoxide over a 10 minute period at 25° C. After standing at room temperature, the reaction is quenched with half-saturated brine and brought to pH 4 with 4N HCl. The product is extracted with an ether-hexane mixture, and the extract is washed successively with water and brine, dried over $MgSO_4$, and concentrated. The crude product is fractionated with a spinning band column to give a colorless distillate, b.p. 121°–122° C., IR 3270, 2110 and 1645 $cm^{-1}$.

EXAMPLE 91

Preparation of ethyl 9-oxo-13-trans-17-cis-prostadienoate

In the manner described in Example 85, 2-(6-carbethoxyhexyl)-2-cyclopentenone (Example 13) is added to the reagent prepared from cis-5-octen-1-yne (Example 90), diisobutylaluminum hydride, and n-butyl lithium. The crude product, obtained by acid hydrolysis and evaporation of the organic solvent, is purified by distillation to give an oil, IR 1740 $cm^{-1}$ (ester and ketone carbonyls) and 967 $cm^{-1}$ (trans-vinyl group).

EXAMPLE 92

Preparation of ethyl 9-oxo-6,7-dinor-13-trans-prostenoate

In the manner described in Example 80, 2-(4-carbethoxybutyl)-2-cyclopentenone (Example 15) is added to the reagent prepared from 1-octyne, diisobutylaluminum hydride, and methyl lithium. The product is obtained by acid hydrolysis, ether extraction and distillation to yield a colorless oil, b.p. 149°–150° C. (0.075 mm.). IR 1740 $cm^{-1}$ (ester and ketone carbonyls) 963 $cm^{-1}$ (trans-vinyl group).

EXAMPLE 93

Preparation of ethyl 20-chloro-9-oxo-6,7-dinor-13-trans prostenoate

In the manner described in Example 85, 2-(4-carbethoxybutyl)-2-cyclopentenone (Example 15) is added to the reagent prepared from 8-chloro-1-octyne, diisobutylaluminum hydride, and n-butyl lithium. The crude product obtained by acid hydrolysis and ether extraction is purified by silica gel chromatography to give an oil, IR 1740 $cm^{-1}$ (ester and ketone carbonyls) 967 $cm^{-1}$ (trans-vinyl group).

EXAMPLE 94

Preparation of ethyl 9-oxo-6,7,20-trinor-13-trans-prostenoate

In the manner described in Example 80 2-(4-carbethoxybutyl)-2-cyclopentenone (Example 15) is added to the reagent prepared from 1-heptyne, diisobutylaluminum hydride and methyl lithium. The crude product obtained by acid hydrolysis and ether extraction is purified by silica gel chromatography to give an oil, IR 1740 $cm^{-1}$ (ester and ketone carbonyls) 967 $cm^{-1}$ trans-vinyl group).

EXAMPLE 95

Preparation of ethyl 9-oxo-6,7-dinor-13-trans-17-cis-prostadienoate

In the manner described in Example 91, 2-(4-carbethoxybutyl)-2-cyclopentenone (Example 15) is added to the reagent prepared from cis-5-octen-1-yne (Example 54), diisobutylaluminum hydride, and n-butyl lithium. The crude product obtained by acid hydrolysis and ether extraction is purified by silica gel chromatography to give an oil, IR 1740 $cm^{-1}$ (ester and ketone carbonyls) 967 $cm^{-1}$ (trans-vinyl group).

EXAMPLE 96

Preparation of ethyl 20-chloro-9-oxo-6,7,17,18,19-pentanor-13-trans-prostenoate

In the manner described in Example 85, 2-(4-carbethoxybutyl)-2-cyclopentenone (Example 15) is added to the reagent prepared from 5-chloro-1-pentyne, diisobutylaluminum hydride, and n-butyl lithium. The crude product obtained by acid hydrolysis and ether extraction is purified by silica gel chromatography to given an oil, IR 1740 $cm^{-1}$ (ester and ketone carbonyls), 967 $cm^{-1}$ (trans-vinyl group).

EXAMPLE 97

Preparation of ethyl 17-methyl-9-oxo-6,7,19,20-tetranor-13-trans-prostenoate

In the manner described in Example 85, 2-(4-carbethoxybutyl)-2-cyclopentenone (Example 15) is added to the reagent prepared from 5-methyl-1-hexyne, diisobutylaluminum hydride and n-butyl lithium. The crude product obtained by acid hydrolysis and ether extraction is purified by silica gel chromatography to give an oil, IR 1740 $cm^{-1}$ (ester and ketone carbonyls), 967 $cm^{-1}$ (trans-vinyl group).

EXAMPLE 98

Preparation of ethyl 9-oxo-13-propyl-6,7,18,19,20-pentanor-13-trans-prostenoate

In the manner described in Example 80, 2-(4-carbethoxybutyl)-2-cyclopentenone (Example 15) is added to the reagent prepared from 4-octyne, diisobutylaluminum hydride, and methyl lithium. The crude product obtained by acid hydrolysis and ether extraction is purified by silica gel chromatography to give an oil, IR 1740 $cm^{-1}$ (ester and ketone carbonyls).

EXAMPLE 99

Preparation of ethyl 9-oxo-5,6,7-trinor-13-trans-prostenoate

In the manner described in Example 80, 2-(3-carbethoxypropyl)-2-cyclopentenone (Example 14) is added to the reagent prepared from 1-octyne, diisobutylaluminum hydride and methyl lithium. The crude product obtained by acid hydrolysis and ether extraction is purified by silica gel chromatography to give an oil, IR 1740 $cm^{-1}$ (ester and ketone carbonyls), 967 $cm^{-1}$ (trans-vinyl group).

EXAMPLE 100

Preparation of ethyl 9-oxo-20-propyl-5,6,7-trinor-13-trans-prostenoate

In the manner described in Example 80, 2-(3-carbethoxypropyl)-2-cyclopentenone (Example 14) is added to the reagent prepared from 1-undecyne, diisobutylaluminum hydride and methyl lithium. The crude product obtained by acid hydrolysis and ether extraction is purified by silica gel chromatography to give an oil, IR 1740 cm$^{-1}$ (ester and ketone carbonyls), 967 cm$^{-1}$ (trans-vinyl group).

EXAMPLE 101

Preparation of ethyl 9-oxo-5,6,7,18,19,20-hexanor-13-trans-prostenoate

In the manner described in Example 80, 2-(3-carbethoxypropyl)-2-cyclopentenone (Example 14) is added to the reagent prepared from 1-pentyne, diisobutylaluminum hydride and methyl lithium. The crude product obtained by acid hydrolysis and ether extraction is purified by silica gel chromatography to give an oil, IR 1740 cm$^{-1}$ (ester and ketone carbonyls), 967 cm$^{-1}$ (trans-vinyl group).

EXAMPLE 102

Preparation of ethyl 20-chloro-9-oxo-5,6,7-trinor-13-trans-prostenoate

In the manner described in Example 80, 2-(3-carbethoxypropyl)-2-cyclopentenone (Example 14) is added to the reagent prepared from 8-chloro-1-octyne, diisobutylaluminum hydride, and methyl lithium. The crude product obtained by acid hydrolysis and ether extraction is purified by silica gel chromatography to give an oil, IR 1740 cm$^{-1}$ (ester and ketone carbonyls), 967 cm$^{-1}$ (trans-vinyl group).

EXAMPLE 103

Preparation of ethyl 9-oxo-7a,7b-bis-homo-13-trans-prostenoate

In the manner described in Example 80, 2-(8-carbethoxyoctyl)-2-cyclopentenone (Example 23) is added to the reagent prepared from 1-octyne, diisobutylaluminum hydride, and methyl lithium. The crude product obtained by acid hydrolysis and ether extraction is purified by silica gel chromatography to give an oil, IR 1740 cm$^{-1}$ (ester and ketone carbonyls), 967 cm$^{-1}$ (trans-vinyl group).

EXAMPLE 104

Preparation of ethyl 20-chloro-9-oxo-7a,7b-bis-homo-17,18,19-trinor-13-trans-prostenoate In the manner described in Example 85, 2-(8-carbethoxyoctyl)-2-cyclopentenone (Example 23) is added to the reagent prepared from 5-chloro-1-pentyne, diisobutylaluminum hydride, and n-butyl lithium. The crude product obtained by acid hydrolysis and ether extraction is purified by silica gel chromatography to give an oil, IR 1740 cm$^{-1}$ (ester and ketone carbonyls), 967 cm$^{-1}$ (trans-vinyl group).

EXAMPLE 105

Preparation of ethyl 20-butyl-9-oxo-7a,7b-bis-homo-13-trans-prostenoate

In the manner described in Example 80, 2-(8-carbethoxyoctyl)-2-cyclopentenone (Example 23) is added to the reagent prepared from 1-dodecyne, diisobutylaluminum hydride, and methyl lithium. The crude product obtained by acid hydrolysis and ether extraction is purified by silica gel chromatography to give an oil, IR 1740 cm$^{-1}$ (ester and ketone carbonyls), 967 cm$^{-1}$ (trans-vinyl group).

EXAMPLE 106

Preparation of ethyl 15-methyl-9-oxo-7a,7b-bis-homo-17,18,19,20-tetranor-13-trans-prostenoate In the manner described in Example 80, 2-(8-carbethoxyoctyl)-2-cyclopentenone (Example 23) is added to the reagent prepared from 3-methyl-1-butyne, diisobutylaluminum hydride, and methyl lithium. The crude product obtained by acid hydrolysis and ether extraction is purified by silica gel chromatography to give an oil, IR 1740 cm$^{-1}$ (ester and ketone carbonyls), cm$^{-1}$ (trans-vinyl group).

EXAMPLE 107

Preparation of ethyl 20-iodo-9-oxo-17,18,19-trinor-13-trans-prostenoate

A stirred mixture of 51.5 g. of ethyl 20-chloro-9-oxo-17,18,19-trinor-13-trans-prostenoate Example 88), 30 g. of sodium iodide, and 250 ml. of acetone is refluxed for 10 hours. An additional 10 g. of sodium iodide is added, and the reaction is continued for 2 hours. The reaction mixture is filtered, concentrated to a volume of 150 ml., diluted with water, and extracted with ether. The extract is washed with saturated sodium chloride, dried, and evaporated to give an oil.

EXAMPLE 108

Preparation of ethyl 20-iodo-9-oxo-13-trans-prostenoate

A stirred mixture of 30 g. of ethyl 20-chloro-9-oxo-13-trans-prostenoate (Example 84), 25 g. of sodium iodide and 225 ml. of acetone is refluxed for 12 hours. The reaction mixture is concentrated, diluted with water, and extracted with ether. The extract is washed with saturated sodium chloride, dried, and evaporated to give an oil.

EXAMPLES 109–112

Treatment of the corresponding 20-chloroprostenoate or 20-chloro-17,18,19-trinor-prostenoate with sodium iodide in acetone by the procedure of Example 107 provides the 20-iodo derivatives of Table IV below.

TABLE IV

| Example | Starting 20-Chloro-Derivative of Example | Product |
|---|---|---|
| 109 | 93 | ethyl 20-iodo-9-oxo-6,7-dinor-13-trans-prostenoate |
| 110 | 96 | ethyl 20-iodo-9-oxo-6,7-17,18,19-pentanor-13-trans-prostenoate |
| 111 | 102 | ethyl 20-iodo-9-oxo-5,6,7-trinor-13-trans- |

TABLE IV-continued

| Example | Starting 20-Chloro-Derivative of Example | Product |
|---|---|---|
| 112 | 104 | prostenoate ethyl 20-iodo-9-oxo-7a,7b,-dihomo-17,18,19-trinor-13-trans-prostenoate |

EXAMPLE 113

Preparation of ethyl 9-oxo-18-thia-13-trans-prostenoate

To 6.0 ml. of a stirred, ice-cold solution of 0.5M 5-ethylisothiouronium iodide in 10:1 ethanol:water is added 264 mg. of sodium hydroxide dissolved in 2.0 ml. of ethanol and 4.0 ml. of water. The mixture is stirred under nitrogen at ambient temperature for 15 min. and then cooled in the ice bath while a solution of ethyl 20-iodo-9-oxo-17,18,19-trinor-13-trans-prostenoate (434 mg.) (Example 107) in 3 ml. of ethanol is added. The reaction mixture is stirred successively at 0° for 15 min., at ambient temperature for 15 min., and at 40° for 5 min. The mixture is diluted with water and extracted with ether. The extract is washed successively with water and saturated sodium chloride, dried, and evaporated. The crude product is purified by chromatography on silica gel to give an oil, IR 1740 cm$^{-1}$ (ester and ketone carbonyls) and 967 cm$^{-1}$ (trans vinyl group); NMR (CCl$_4$) δ2.47 ppm (multiplet, methylenethio groups).

EXAMPLES 114–115

Treatment according to the procedure of Example 113, of the various 20-iodo-17,18,19-trinor-trans-prostenoates of Table V (below) with sodium ethyl mercaptide (prepared in situ as in Example 113) is productive of the various 18-thia-prostenoates of the Table.

TABLE V

| Example | Starting 20-Iodoprostenoate of Example | Product 18-Thiaprostenoate |
|---|---|---|
| 114 | 110 | ethyl 9-oxo-18-thia-6,7-dinor-13-trans-prostenoate |
| 115 | 112 | ethyl 9-oxo-18-thia-7a, 7b-bis-homo-13-trans-prostenoate |

EXAMPLE 116

Preparation of ethyl 9-oxo-18-oxythia-13-trans-prostenoate

To a stirred, ice-cold solution of the 18-thiaprostenoate of Example 113 (11.5 g., 31 mmole) in 150 ml. of ethanol is added a solution of sodium metaperiodate (6.65 g., 31.2 mmole) in 55 ml. of water during a twenty min. period. The mixture is allowed to stand at 10° C. for 17 hours. Excess periodate is destroyed by the addition of one ml. of ethylene glycol, and the mixture is filtered. The filtrate is concentrated to one-third of the original volume, diluted with water, and extracted with ether. The extract is washed with brine, dried over MgSO$_4$, and concentrated. Column chromatography of the residue on silica gel with chloroform-ether mixture gives an oil, IR 1740 (ester and ketone carbonyls), 1040 (sulfoxide), and 967 cm$^{-1}$ (trans vinyl group).

EXAMPLE 117

Preparation of ethyl 9-oxo-18-oxythia-7a,7b-bis-homo-13-trans-prostenoate

Treatment of the sulfide of Example 115 with sodium metaperiodate by the procedure of Example 116 is productive of the subject sulfoxide.

EXAMPLE 118

Preparation of ethyl 20,20-dicarbethoxy-9-oxo-18,19-dinor-13-trans-prostenoate

To a solution of sodium ethoxide, prepared from 426 mg. of sodium, in 20 ml. of ethanol is added a solution of 3.96 g. of diethyl malonate in 10 ml. of ethanol over a 10 min. period. After stirring for 45 min., a solution containing 5.21 g. of ethyl 20-iodo-9-oxo-17,18,19-trinor-13-trans-prostenoate (Example 107) in 10 ml. of ethanol is added, and the resulting solution is refluxed for 16 hours. The solution is concentrated to one-third of the original volume, diluted with 50 ml. of ether, and treated with 40 ml. of 0.2N HCl. The ether phase is washed with brine, dried over MgSO$_4$, and concentrated. Column chromatography of the residue on silica gel with chloroform-ether mixtures gives an oil, IR 1740 (ester and ketone carbonyls) and 967 cm$^{-1}$ (trans vinyl group); nmr 3.2δ(triplet, alkyl-malonate methine hydrogen)

EXAMPLE 119

Preparation of ethyl 20,20-dicarbethoxy-9-oxo-6,7,18,19-tetranor-13-trans-prostenoate Treatment of the ethyl 20-iodo-9-oxo-6,7,17,18,19-pentanor-13-trans-prostenoate of Example 110 with diethyl sodio malonate by the procedure of Example 118 is productive of the product.

EXAMPLE 120

Preparation of ethyl 9,9-ethylenedioxy-20-iodo-17,18,19-trinor-13-trans-prostenoate A solution of 25.2 g. of ethyl 20-iodo-9-oxo-17,18,19-trinor-13-trans-prostenoate (Example 107), 5.6 ml. of ethylene glycol and 110 mg. of p-toluenesulfonic acid monohydrate in 170 ml. of benzene is refluxed for 4 hours with azeotropic removal of water. The solution is concentrated to a volume of 50 ml. Column chromatography of the solution on Florisil with benzene gives a liquid, IR 1740 (ester carbonyl), 967 (trans vinyl group), and 952 cm$^{-1}$ (ethylene ketal).

EXAMPLES 121–122

Ketalization with ethylene glycol in the presence of p-toluenesulfonic acid of appropriate 20-iodo-9-oxo-prostenoates by the procedure of Example 120 provides the ketals of Table VI, which follows.

TABLE VI

| Example | Starting Ketone of Example | Product |
|---|---|---|
| 121 | 110 | ethyl 9,9-ethylenedioxy-20-iodo-6,7,17,18,19-pentanor-13-trans- |

TABLE VI-continued

| Example | Starting Ketone of Example | Product |
| --- | --- | --- |
| 122 | 108 | prostenoate ethyl 9,9-ethylenedioxy-20-indo-13-trans-prostenoate |

EXAMPLE 123

Preparation of ethyl 9,9-ethylenedioxy-18-oxa-13-trans-prostenoate

To a stirred, ice-cold suspension of 1.68 g. of 57% sodium hydride in oil and 20 ml. of dimethylformamide (DMF) is added a solution of 2.5 ml. of ethanol in 5 ml. of DMF over a 15 min. period. The mixture evolves gas and is stirred at room temperature for 45 min. To the resulting suspension is added a solution of 9.57 g. of ethyl 9,9-ethylenedioxy-20-iodo-17,18,19-trinor-13-trans-prostenoate (Example 120) in 15 ml. of DMF over a 10 min. period at 10°–15° C. The resulting dark mixture is stirred at ambient temperature for 45 min. and then poured into 200 ml. of ice water. The mixture is brought to pH 7 with 4N HCl and extracted with ether. The extract is washed with brine, dried over MgSO$_4$, and concentrated. Column chromatography of the residue on silica gel with benzene-ether mixtures gives a liquid, IR 1740 (ester carbonyl), 967 (trans vinyl group), and 952 cm$^{-1}$ (ethylene ketal); nmr 3.4δ(triplet superimposed on quartet, O-methylene ether groups).

EXAMPLE 124

Preparation of ethyl 9,9-ethylenedioxy-20-phthalimido-13-trans-prostenoate

A stirred mixture of 8.80 g. of ethyl 9,9-ethylenedioxy-20-iodo-13-trans-prostenoate (Example 122), 3.28 g. of potassium phthalimide, and 25 ml. of DMF is heated at 70° C. for 2 hours. The cooled mixture is diluted with water and extracted with ether. The extract is washed with brine, dried over potassium bicarbonate, and concentrated to give an oil, IR 1770 (phthalimide group), 1735 (ester carbonyl group), 1710 (phthalimide group), 967 (trans vinyl group), and 950 cm$^{-1}$ (ethylene ketal).

EXAMPLE 125

Preparation of 20-amino-9-oxo-13-trans-prostenoic acid hydrochloride

A stirred mixture of 9.3 g. of ethyl 9,9-ethylenedioxy-20-phthalimido-13-trans-prostenoate (Example 124), 2.25 g. of potassium hydroxide, 85 ml. of methanol, and 1.0 ml. of water is refluxed for 2 hours. After addition of 2.25 g. of potassium hydroxide and 2.0 ml. of water, the mixture is refluxed for an additional one hour. The solution is concentrated to remove methanol, and the residue is refluxed with 75 ml. of 4N HCl for 18 hours. The upper phase of the resulting two-phase system is dissolved in water and concentrated to give an oil, IR 1730 (ketone carbonyl group), 1710 (acid carbonyl group), and 967 cm$^{-1}$ (trans vinyl group).

EXAMPLE 126

Preparation of ethyl 9,9-ethylenedioxy-20-pyrrolidino-17,18,19-trinor-13-trans-prostenoate A mixture of 4.17 g. of potassium carbonate, 9.95 g. of pyrrolidine, and 55 ml. of dimethylformamide (DMF) is stirred at 50° C. To the mixture is added a solution of 13.5 g. of ethyl 9,9-ethylenedioxy-20-iodo-17,18,19-trinor-13-trans-prostenoate (Example 120) in 15 ml. of DMF over a 40 min. period. After an additional 30 min. at 50° C. the mixture is cooled and treated with 200 ml. of water. The mixture is extracted with 5:1 (v/v) ether:hexane. The extract is washed with brine, dried with potassium carbonate, and concentrated. Column chromatography of the residue on Florisil with benzene-ether mixtures gives an oil, IR 1740 (ester carbonyl group), 967 (trans vinyl group), and 950 cm$^{-1}$ (ethylene ketal).

EXAMPLES 127–129

Treatment of the iodoprostenoate ketals of Table VII (below) by the procedure of Example 126 with the indicated amine is productive of the aminoprostenoate ketals of the table.

TABLE VII

| Example | Starting Iodoprostenoate of Example | Amine | Aminoprostenoate Product |
| --- | --- | --- | --- |
| 127 | 121 | piperidine | ethyl 9,9-ethylenedioxy-20-piperidino-6,7,17,18,19-pentanor-13-trans-prostenoate |
| 128 | 120 | morpholine | ethyl 9,9-ethylenedioxy-20-morpholino-17,18,19-trinor-13-trans-prostenate |
| 129 | 122 | pyrrolidine | ethyl 9,9-ethylenedioxy-20-pyrrolidino-13-trans-prostenoate |

EXAMPLE 130

Preparation of 20-mercapto-9-oxo-13-trans-prostenoic acid

A solution of 9.53 g. of ethyl 20-iodo-9-oxo-13-trans-prostenoate (Example 108) and 1.60 g. of thiourea in 20 ml. of ethanol is refluxed for 45 min. The resulting solution of the corresponding 20-S-isothiouronium salt is diluted with 140 ml. of methanol and a solution of 5.30 g. of potassium hydroxide in 20 ml. of water. The resulting solution is allowed to stand at room temperature for 19 hours. The solution is concentrated to a volume of 100 ml. and diluted with 200 ml. of water. The solution is acidified with 4N HCl and extracted with ether. The extract is washed with brine, dried over MgSO$_4$, and concentrated. Column chromatography of the residue on silica gel with chloroform-ether mixtures gives an oil, IR 1740 (ketone carbonyl), 1710 (acid carbonyl), and 967 cm$^{-1}$ (trans vinyl group); mnr 2.4 δ (methylene thiol group).

EXAMPLE 131

Preparation of 20-mercapto-9-oxo-6,7-dinor-13-trans-prostenoic acid

Treatment of the 20-iodoprostenoate of Example 109 according to the procedure of Example 130, with thiourea produces the corresponding 20-S-isothiouronium salt, which on treatment with sodium hydroxide solution is productive of the 20-mercapto derivative.

EXAMPLE 132

Preparation of 9-oxo-20-pyrrolidino-17,18,19-trinor-13-trans-prostenoic acid A stirred mixture of 9.20 g. of ethyl, 9,9-ethylenedioxy-20-pyrrolidino-17,18,19-trinor-13-trans-prostenoate (Example 126), 0.02 ml. of concentrated sulfuric acid, 35 ml. of glacial acetic acid, and 17.5 ml. of water is refluxed for 17 hours. The cooled reaction mixture is treated with 58 mg. of sodium bicarbonate and concentrated to near-dryness. The residue is treated with water and extracted with ether. The ether phase is back-extracted with 0.1N HCl, and all aqueous phases are concentrated to give the subject amino acid.

EXAMPLES 133–135

Hydrolysis of the aminoprostenoate ketals of Table VIII below by the procedure of Example 132 is productive of the amino-prostenoic acids of the table.

TABLE VIII

| Example | Starting Aminoprostenoate Ketal of Example | Product Aminoprostenoic Acid |
| --- | --- | --- |
| 133 | 127 | 9-oxo-20-piperidino-6,7,17,18,19-pentanor-13-trans-prostenoic acid |
| 134 | 128 | 20-morpholino-9-oxo-17,18,19-trinor-13-trans-prostenoic acid |
| 135 | 129 | 9-oxo-20-pyrrolidino-13-trans-prostenoic acid |

EXAMPLES 136–141

Treatment of 2-(6-carbethoxyoctyl)-2-cyclopentenone (Example 31) in the manner of Example 80 with the reagents prepared from the alkyne indicated in Table IX below, diisobutyl aluminum hydride and methyl lithium is productive of the prostenoate esters of the first three Examples of this table. Saponification of the ester by the procedure of Example 151 provides the corresponding prostenoic acids.

TABLE IX

| Example | Starting Alkyne or Prostenoate Ester | Product |
| --- | --- | --- |
| 136 | 1-octyne | ethyl 2-ethyl-9-oxo-13-trans-prostenoate |
| 137 | cis-5-octen-1-yne | ethyl 2-ethyl-9-oxo-13-trans-17-cis-prostadienoate |
| 138 | 8-chloro-1-octyne | ethyl 2-ethyl-9-oxo-20-chloro-13-trans-prostenoate |
| 139 | Example 136 | 2-ethyl-9-oxo-13-trans-prostenoic acid |
| 140 | Example 137 | 2-ethyl-9-oxo-13-trans-17-cis-prostadienoic acid |
| 141 | Example 138 | 2-ethyl-9-oxo-20-chloro-13-trans-prostenoic acid |

EXAMPLE 142

Preparation of ethyl 9α- and 9β-hydroxy-13-trans-prostenoate

A solution of 1 g. of ethyl 9-oxo-13-trans-prostenoate (Example 80) in 40 ml. of absolute alcohol containing 41 mg. of sodium borohydride is stirred at room temperature (protected from moisture) for 19 hours. The mixture is poured into 100 ml. of water and the resulting solution is extracted several times with ether. The combined ether extracts are washed several times with saturated sodium chloride solution, dried with anhydrous magnesium sulfate and taken to dryness to give 806 mg. of an oil. Distillation furnished 700 mg. (70%) of product as a pale yellow oil; b.p. 179° C. (0.13 mm); $\lambda_{max}$ 2.98, 5.78, 5.81 (shoulder), 8.50, 10.30 $\mu$; nmr 2H multiplet $\delta$5.36 (olefinic protons), 2H triplet 4.13 ($OCH_2$ of ester), 3H distorted triplet 1.23 (methyl of ester) and 3H distorted triplet 0.90 (terminal methyl).

EXAMPLES 143–150

The following alcohols (as mixtures of 9α- and 9β-epimers) of Table X are prepared by sodium borohydride reduction of the corresponding 9-ketones according to the procedure of Example 142.

TABLE X

| Example | Starting Ketone of Example | Product |
| --- | --- | --- |
| 143 | 88 | ethyl 9-hydroxy-20-chloro-17,18,19-trinor-13-trans-prostenoate |
| 144 | 87 | ethyl 9-hydroxy-17-methyl-18,19-dinor-13-trans-prostenoate |
| 145 | 92 | ethyl 9-hydroxy-6,7-dinor-13-trans-prostenoate |
| 146 | 102 | ethyl 9-hydroxy-20-chloro-5,6,7-trinor-13-trans-prostenoate |
| 147 | 105 | ethyl 9-hydroxy-20-butyl-7a,7b-bis-homo-13-trans-prostenoate |
| 148 | 113 | ethyl 9-hydroxy-18-thia-13-trans-prostenoate |
| 149 | 106 | ethyl 9-hydroxy-15-methyl-7a,7b-bis-homo-17,18,19,20-tetranor-13-trans-prostenoate |
| 150 | 89 | ethyl 9-hydroxy-13-propyl-18,19,20-trinor-13-trans-prostenoate |

EXAMPLE 151

Preparation of 20-butyl-9-oxo-13-trans-prostenoic acid

A solution of 2.33 g. of ethyl 20-butyl-9-oxo-13-trans-prostenoate (Example 81) and 1.30 g. of potassium hydroxide in 35 ml. of methanol and 3.5 ml. of water is allowed to stand at room temperature for 24 hours. The reaction mixture is concentrated in vacuo, diluted with water, and washed with ether. The aqueous phase is acidified to pH 2 and extracted with ether. The extract is washed with saturated sodium chloride, dried, and evaporated to give an oil, IR 1745 cm$^{-1}$ (ketone carbonyl), 1710 cm$^{-1}$ (acid carbonyl), and 967 cm$^{-1}$ (trans vinyl group).

EXAMPLE 152

Preparation of 9-oxo-13-trans-prostenoic acid

A mixture of 0.140 g. of ethyl 9-oxo-13-trans-prostenoate (Example 80) and 0.072 g. of potassium hydroxide in 6 ml. of 1:1 aqueous methanol is stirred at ambient temperature for 17 hours. The resulting solution is acidified with hydrochloric acid, extracted with diethyl ether, and the organic phase is washed with water and saturated brine, dried, and the solvent removed to yield 0.128 g. of an oil, IR 1739 cm$^{-1}$ (ketone carbonyl) 1706 cm$^{-1}$ (acid carbonyl), 969 cm$^{-1}$ (trans vinyl group); NMR (CDCl$_3$) 5.34–5.67 (multiplet, 2H, vinyl protons, J trans=15 Hz), 10.47 (broad singlet, 1H, carboxyl proton, exchangeable); Mass spectrum, parent peak at 322 m$\mu$.

EXAMPLE 153

Preparation of 9-oxo-6,7-dinor-13-trans-prostenoic acid

In the manner described in Example 152, ethyl 9-oxo-6,7-dinor-13-trans-prostenoate (Example 92) is saponified with potassium hydroxide, acidified, and worked-up by ether extraction and evaporative distillation at 160° C. (0.005 Torr) to yield a colorless oil.

EXAMPLE 154

Preparation of 9$\alpha$- and 9$\beta$-hydroxy-13-trans-prostenoic acid

A suspension of 1.8 g. of ethyl 9$\alpha$- and 9$\beta$-hydroxy-13-trans-prostenoate (Example 142) in 40 ml. of aqueous methanol (1:1) containing 890 mg. of potassium hydroxide is stirred at ambient temperature for 18 hours. The resulting solution is cooled, acidified with 1N hydrochloric acid and extracted several times with ether. The combined ether extracts are washed with sodium chloride solution, dried with anhydrous magnesium sulfate, and taken to dryness to give 1.61 g. (98%) of product as an oil; $\lambda_{max}$ 2.95, 3.40, 3.75, 5.85, 10.31 $\mu$; nmr 2H singlet $\delta$ 6.10 (hydroxyl and carboxyl protons), 2H multiplet 5.40 (olefinic protons), and 3H distorted triplet 0.90 (terminal methyl).

EXAMPLES 155–190

In the manner described in Example 151, the carboxylic acids of Table XI (below) are prepared by saponification of the corresponding ethyl esters at room temperature in methanol-water followed by acidification and extraction with ether. Infrared characterization of the cyclopentanone derivatives gives bands at about 1745 cm$^{-1}$ (ketone carbonyl), 1710 cm$^{-1}$ (acid carbonyl) and 967 cm$^{-1}$ (trans vinyl group).

TABLE XI

| Example | Starting Ester of Example | Product |
|---|---|---|
| 155 | 82 | 9-oxo-18,19,20-trinor-13-trans-prostenoic acid |
| 156 | 83 | 15-methyl-9-oxo-17,18,19,20-tetranor-13-trans-prostenoic acid |
| 157 | 84 | 20-chloro-9-oxo-13-trans-prostenoic acid |
| 158 | 85 | 9-oxo-20-nor-13-trans-prostenoic acid |
| 159 | 86 | 20-methyl-9-oxo-13-trans-prostenoic acid |
| 160 | 87 | 17-methyl-9-oxo-19,20-dinor-13-trans-prostenoic acid |
| 161 | 88 | 20-chloro-9-oxo-17,18,19-trinor-13-trans-prostenoic acid |
| 162 | 89 | 9-oxo-13-propyl-18,19,20-trinor-13-trans-prostenoic acid |
| 163 | 91 | 9-oxo-13-trans-17-cis-prostadienoic acid |
| 164 | 93 | 20-chloro-9-oxo-6,7-dinor-13-trans-prostenoic acid |
| 165 | 94 | 9-oxo-6,7,20-trinor-13-trans-prostenoic acid |
| 166 | 95 | 9-oxo-6,7-dinor-13-trans-17-cis-prostadienoic acid |
| 167 | 96 | 20-chloro-9-oxo-6,7,17,18,19-pentanor-13-trans-prostenoic acid |
| 168 | 97 | 17-methyl-9-oxo-6,7,19,20-tetranor-13-trans-prostenoic acid |
| 169 | 98 | 9-oxo-13-propyl-6,7,18,19,20-pentanor-13-trans-prostenoic acid |
| 170 | 99 | 9-oxo-5,6,7-trinor-13-trans-prostenoic acid |
| 171 | 100 | 9-oxo-20-propyl-5,6,7-trinor-13-trans-prostenoic acid |
| 172 | 101 | 9-oxo-5,6,7,18,19,20-hexanor-13-trans-prostenoic acid |
| 173 | 102 | 20-chloro-9-oxo-5,6,7-trinor-13-trans-prostenoic acid |
| 174 | 103 | 9-oxo-7a,7b-bis-homo-13-trans-prostenoic acid |
| 175 | 104 | 20-chloro-9-oxo-7a,7b-bis-homo-17,18,19-trinor-13-trans-prostenoic acid |
| 176 | 105 | 20-butyl-9-oxo-7a,7b-bis-homo-13-trans-prostenoic acid |
| 177 | 106 | 15-methyl-9-oxo-7a,7b-bis-homo-17,18,19,20-tetranor-13-trans-prostenoic acid |
| 178 | 113 | 9-oxo-18-thia-13-trans-prostenoic acid |
| 179 | 114 | 9-oxo-18-thia-6,7-dinor-13-trans-prostenoic acid |
| 180 | 115 | 9-oxo-18-thia-7a,7b-bis-homo-13-trans-prostenoic acid |
| 181 | 116 | 9-oxo-18-oxythia-13-trans-prostenoic acid |
| 182 | 117 | 9-oxo-18-oxythia-7a,7b-bis-homo-13-trans-prostenoic acid |
| 183 | 143 | 9-hydroxy-20-chloro-17,18,19-trinor-13-trans-prostenoic acid |
| 184 | 144 | 9-hydroxy-17-methyl-18,19-dinor-13-trans-prostenoic acid |
| 185 | 145 | 9-hydroxy-6,7-dinor-13-trans-prostenoic acid |
| 186 | 146 | 9-hydroxy-20-chloro-5,6,7-trinor-13-trans-prostenoic acid |
| 187 | 147 | 9-hydroxy-20-butyl-7a,7b-bis-homo-13-trans-prostenoic acid |
| 188 | 148 | 9-hydroxy-18-thia-13- |

TABLE XI-continued

| Example | Starting Ester of Example | Product |
|---|---|---|
| 189 | 149 | trans-prostenoic acid 9-hydroxy-15-methyl-7a,7b-bis-homo-17,18,-19,20-tetranor-13-trans-prostenoic acid |
| 190 | 150 | 9-hydroxy-13-propyl-18,-19,20-trinor-13-trans-prostenoic acid |

EXAMPLE 191

Preparation of 20-carboxy-9-oxo-18,19-dinor-13-trans-prostenoic acid

A solution of ethyl 20,20-dicarbethoxy-9-oxo-18,19-dinor-13-trans-prostenoate (Example 118), prepared from 10.42 g. of iodo compound (Example 107), is dissolved in 240 ml. of methanol and treated with a solution of 9.50 g. of potassium hydroxide in 24 ml. of water. The solution is allowed to stand at room temperature for 42 hours. Most of the methanol is removed in vacuo, and the residue is dissolved in 200 ml. of water. After acidification with 4N HCl the acidic product is extracted with ether. The extract is washed with brine, dried over MgSO$_4$, and evaporated. The residue is heated at 120° C. for 1.5 hours and subjected to column chromatography on silica gel with chloroform ether mixtures to give an oil, IR 1745 cm$^{-1}$ (ketone carbonyl), 1715 cm$^{-1}$ (acid carbonyl), and 967 cm$^{-1}$ (trans vinyl group).

EXAMPLE 192

Preparation of 20-carboxy-9-oxo-6,7,18,19-tetranor-13-transprostenoic acid

Hydrolysis and decarboxylation, according to the procedure of Example 191, of ethyl 20,20-dicarbethoxy-9-oxo-6,7,18,19-tetranor-13-trans-prostenoate (Example 119) provides the product.

EXAMPLE 193

Preparation of ethyl 18-oxa-9-oxo-13-trans-prostenoate

A solution of 1.07 g. of ethyl 9,9-ethylenedioxy-18-oxa-13-trans-prostenoate (Example 123) and 27 mg. of p-toluenesulfonic acid monohydrate in 10 ml. of acetone is allowed to stand at room temperature for 17 hours. The bulk of the acetone is evaporated, and the residue is treated with 25 ml. of water and extracted with ether. The extract is washed successively with dilute NaHCO$_3$ and brine and dried over MgSO$_4$. Evaporation of the solvent gives an oil, IR 1740 (ester and ketone carbonyls) and 967 cm$^{-1}$ (trans vinyl group).

EXAMPLE 194

Preparation of 18-oxa-9-oxo-13-trans-prostenoic acid

Saponification of ethyl 18-oxa-9-oxo-13-trans-prostenoate (Example 193) by the procedure of Example 151 is productive of the product.

EXAMPLE 195

Preparation of 3'-pyridyl 9-oxo-13-trans-prostenoate

9-Oxo-13-trans-prostenoic acid (Example 152) is converted to 9-oxo-13-trans-prostenoyl chloride by treatment with thionyl chloride. A benzene solution of 9-oxo-13-trans-prostenoyl chloride (24.8 moles) is slowly added to a slight excess of 3-hydroxypyridine (26 moles) in 100 ml. of benzene containing 5 ml. of triethylamine. The mixture is magnetically stirred and refluxed for 30 min. The reaction mixture is filtered and taken to dryness and the residue is dissolved in ether and washed successively with saline, dilute sodium bicarbonate solution, dried and taken to dryness. The oil is purified by adsorption chromatography on a magnesia-silica gel column and eluted with benzene to give a dark yellow oil.

EXAMPLES 196–197

In the manner described in Example 195, the various prostenoic acids of the following table are converted with thionyl chloride to the corresponding prostenoyl chlorides and thence with the indicated alcohols to the various prostenoic acid esters of Table XII, which follows.

TABLE XII

| Example | Starting Prostenoic Acid of Example | Alcohol | Product |
|---|---|---|---|
| 196 | 171 | methanol | methyl 9-oxo-20-propyl-5,6,7-trinor-13-trans-prostenoate |
| 197 | 152 | n-butnaol | n-butyl 9-oxo-13-trans-prostenoate |

EXAMPLE 198

Preparation of ethyl 9-oxo-3-thia-13-trans-prostenoate

In the manner described in Example 80, treatment of 2-(6-carbethoxy-5-thiahexyl)-2-cyclopentenone (Example 40) with the reagent prepared from 1-octyne, diisobutylaluminum hydride and methyl lithium gives the subject 3-thiaprostenoate as a yellow oil.

EXAMPLE 199

Preparation of ethyl 3-oxa-9-oxo-13-trans-prostenoate

In the same manner as for the preparation of the compound of Example 80, ethyl 3-oxa-9-oxo-13-trans-prostenoate is prepared by the addition of 2-(6-carbethoxy-5-oxahexyl)-2-cyclopentenone (Example 36) to the reagent prepared from 1-octyne, diisobutylaluminum hydride and methyl lithium.

EXAMPLES 200–207

In the manner of Example 80, treatment of the oxa or thia cyclopentenone esters of Examples 36 and 40, respectively, with the alanate complex obtained from the alkynes indicated in Table XIII below, diisobutylaluminum hydride and methyl lithium, is productive of the 3-oxa or 3-thia prostenoates of the Table.

TABLE XIII

| Example | Starting Cyclopentenone | Starting Alkyne | Product |
|---|---|---|---|
| 200 | 2-(6-carbethoxy-5-oxahexyl)-2-cyclopentenone | 8-chloro-1-octyne | ethyl 20-chloro-3-oxa-9-oxo-13-trans-prostenoate |
| 201 | 2-(6-carbethoxy-5-oxahexyl)-2-cyclopentenone | 5-chloro-1-pentyne | ethyl 20-chloro-3-oxa-9-oxo-17,18,19-trinor-13-trans-prostenoate |
| 202 | 2-(6-carbethoxy-5-oxahexyl)-2-cyclopentenone | cis-5-octen-1-yne | ethyl 3-oxa-9-oxo-13-trans-7-cis-prostadienoate |
| 203 | 2-(6-carbethoxy-5-oxahexyl)-2-cyclopentenone | 1-nonyne | ethyl 20-methyl-3-oxa-9-oxo-13-trans-prostenoate |
| 204 | 2-(6-carbethoxy-5-thiahexyl)-2-cyclopentenone | 8-chloro-1-octyne | ethyl 20-chloro-9-oxo-3-thia-13-trans-prostenoate |
| 205 | 2-(6-carbethoxy-5-thiahexyl)-2-cyclopentenone | 5-chloro-1-pentyne | ethyl 20-chloro-9-oxo-3-thia-17,18,19-trinor-13-trans-prostenoate |
| 206 | 2-(6-carbethoxy-5-thiahexyl)-2-cyclopentenone | cis-5-octen-1-yne | ethyl 9-oxo-3-thia-13-trans-17-cis-prostadienoate |
| 207 | 2-(6-carbethoxy-5-thiahexyl)-2-cyclopentenone | 1-hexyne | ethyl 9-oxo-3-thia-19,20-dinor-13-trans-prostenoate |

EXAMPLE 208

Preparation of 2-carbalkoxy(methyl/ethyl)-2-(carbethoxymethyl)-cyclopentan-1-one In the manner described in Example 1, treatment of cyclopentanone-2-carboxylate (mixed methyl and ethyl esters) with sodium hydride in dimethoxyethane followed by ethyl bromoacetate provides a yellow oil, b.p. 130°–131° C. (7 mm).

EXAMPLE 209

Preparation of 2-(carboxymethyl)cyclopentan-1-one

In the manner described in Example 2, the 2-carbalkoxy-2-carbethoxymethylcyclopentanone of Example 208 is decarbalkoxylated to provide 2-carboxymethyl-cyclopentan-1-one.

EXAMPLE 210

Preparation of 2-carbethoxymethylcyclopentan-1-one

In the manner of Example 3, 2-(carboxymethyl)cyclopentan-1-one (Example 209) is esterified to provide the subject ester.

EXAMPLE 211

Preparation of 1-acetoxy-2-(carbethoxymethyl)cyclopent-1-ene

In the manner described in Example 10, treatment of 2-(carbethoxymethyl)cyclopentan-1-one (Example 210) with acetic anhydride and p-toluenesulfonic acid monohydrate gives an oil, b.p. 130°–131° C. (7 mm).

EXAMPLE 212

Preparation of 2-(carbethoxymethyl)cyclopent-2-en-1-one

In the manner described in Example 13, treatment of 1-acetoxy-2-(carbethoxymethyl)cyclopent-1-ene (Example 211) with bromine and subsequent dehydrobromination with lithium bromide-lithium carbonate in N,N-dimethylformamide gives an amber oil. This material is subjected to chromatography on diatomaceous earth using an n-heptane:methyl cellosolve system. Removal of the solvent from hold back volume 4.5–4.7 gives an oil which is then further treated with hydroxylamine hydrochloride, sodium acetate in ethanol at room temperature for 18 hours to give the desired product; b.p. 71° C. (0.12 mm); $\lambda_{max}^{MeOH}$ 222 m$\mu$ (10,300); $\lambda_{max}$ 5.75, 5.85, 6.15, 8.65$\mu$.

EXAMPLE 213

Preparation of ethyl 9-oxo-3,4,5,6,7-pentanor-13-trans-prostenoate

In the manner described in Example 80, 2-(carbethoxymethyl)-2-cyclopentenone (Example 212) is added to the reagent prepared from 1-octyne, diisobutylaluminum hydride and methyl lithium. The crude product obtained by acid hydrolysis and ether extraction is purified by silica gel chromatography to give an oil, IR 1740 cm$^{-1}$ (ester and ketone carbonyls), 967 cm$^{-1}$ (trans-vinyl group).

EXAMPLE 214

Preparation of 2-(carbethoxymethyl)-3-(1-trans-octenyl)-1,1-dioxolano-cyclopentane A mixture of 10.142 g. (0.0362 mole) of 2-(carbethoxymethyl)-3-(1-octenyl)cyclopentanone (ethyl 9-oxo-3,4,5,6,7-pentanor-13-trans-prostenoate, Example 213), 3.49 g. (0.0562 mole) of ethylene glycol, 0.344 g. of p-toluenesulfonic acid monohydrate, and 30 ml. of benzene is refluxed for 4.5 hours with azeotropic removal of water. The mixture is cooled, placed onto a column of 130 g. of Florisil in benzene and the ketal is eluted off with benzene. The filtrate is evaporated to yield 9.53 g. of a colorless oil.

EXAMPLE 215

Preparation of 2-(formylmethyl)-3-(1-trans-octenyl)-1,1-dioxolanocyclopentane

To a solution of 1.00 g. (0.00308 mole) of 2-(carbethoxymethyl)-3-(1-trans-octenyl)-1,1-dioxolano cyclopentane in 5 ml. of heptane at −78° C. and under nitrogen is added dropwise 2.60 ml. of a solution of 25% diisobutylaluminum hydride in hexane. The resulting solution is stirred at −78° C. for 2.5 hours and then poured into cold dilute hydrochloric acid. The organic phase is washed with saturated brine, dried (Na$_2$SO$_4$), and evaporated to yield 0.863 g. of a colorless oil. IR 2695, 1723, 1045, 970 cm$^{-1}$.

EXAMPLE 216

Preparation of 2-(6-carboxy-2-cis-hexenyl)-3-(1-trans-octenyl)-1,1-dioxolano cyclopentane A mixture of 0.194 g. (0.007952 mole) of sodium hydride (free of mineral oil) and 5.5 ml. of dimethylsulfoxide is heated to 70° C. until gas evolution ceases under a nitrogen atmosphere. The resulting solution is cooled below room temperature and treated with a solution of 1.400 g. (0.00316 mole) of 4-carboxybutyl-triphenyl phosphonium bromide [E. J. Corey et al., J. Am. Chem. Soc., 91, 5675 (1969)] in 6 ml. of dimethylsulfoxide. To the resulting red solution is added 0.738 g. (0.00263 mole) of 2-(formylmethyl)-3-(1-trans-octenyl)-1,1-dioxolano cyclopentane in 2 ml. of dimethylsulfoxide and the mixture is stirred at room temperature for 2.25 hours. The mixture is poured into ice water, sodium hydroxide solution is added to pH 12, and the neutral materials are extracted with diethyl ether. The basic phase is acidified with dilute hydrochloric acid and is extracted with diethyl ether. The organic phase is washed with water and saturated brine, dried ($Na_2SO_4$), and evaporated to a semicrystalline mass. The latter is triturated with hot hexane, the solids are filtered off, and the filtrate is evaporated to yield an oil. IR: 1705, 1040, 970, 722 cm$^{-1}$.

EXAMPLE 217

Preparation of 9-oxo-5-cis-13-trans-prostadienoic acid

A solution of 0.726 g. of 2-(6-carboxy-2-cis-hexenyl)-3-(1-trans-octenyl)-1,1-dioxolano cyclopentane and 19 mg. of p-toluenesulfonic acid monohydrate in 30 ml. of acetone is stirred at ambient temperatures for 66 hours. The volatile material is removed in vacuo and the residue is passed through a column of silica gel in chloroform collecting those fractions which contain product. The solvent is evaporated to yield the subject product as an oil. IR: 1740, 1705, 970, 722 cm$^{-1}$.

EXAMPLE 218

Preparation of ethyl 9-oxo-5-cis-13-trans-prostadienoate

By the procedure described in Example 195, 9-oxo-5-cis-13-trans-prostadienoic acid is esterified with ethyl alcohol to the subject ethyl ester.

EXAMPLES 219–226

Treatment of the 9-oxo-13-trans-prostenoate esters of the following Table with sodium borohydride in ethanol by the method described in Example 142 is productive of the 9-hydroxy-(mixture of α and β epimers)-prostenoates of the following Table.

TABLE XIV

| Example | Starting 9-Oxo-prostenoate of Example | Product |
|---|---|---|
| 219 | 199 | ethyl 9-hydroxy-3-oxa-trans-prostenoate |
| 220 | 200 | ethyl 20-chloro-9-hydroxy-3-oxa-13-trans-prostenoate |
| 221 | 202 | ethyl 9-hydroxy-3-oxa-13-trans-17-cis-prostadienoate |
| 222 | 203 | ethyl 9-hydroxy-20-methyl-3-oxa-13-trans-prostenoate |
| 223 | 198 | ethyl 9-hydroxy-3-thia-13-trans-prostenoate |
| 224 | 206 | ethyl 9-hydroxy-3-thia-13-trans-17-cis-prostadienoate |
| 225 | 207 | ethyl 9-hydroxy-3-thia-19,20-dinor-13-trans-prostenoate |
| 226 | 218 | ethyl 9-hydroxy-5-cis-13-trans-prostadienoate |

EXAMPLES 227–244

Saponification of the esters of the following table by the procedure of Example 151 is productive of the carboxylic acids of this table.

TABLE XV

| Example | Starting Ester of Example | Product |
|---|---|---|
| 227 | 198 | 9-oxo-3-thia-13-trans-prostenoic acid |
| 228 | 199 | 9-oxo-3-oxa-13-trans-prostenoic acid |
| 229 | 200 | 20-chloro-3-oxa-9-oxo-13-trans-prostenoic acid |
| 230 | 201 | 20-chloro-3-oxa-9-oxo-17,18,19-trinor-13-trans-prostenoic acid |
| 231 | 202 | 3-oxa-9-oxo-13-trans-17-cis-prostadienoic acid |
| 232 | 203 | 20-methyl-3-oxa-9-oxo-13-trans-prostenoic acid |
| 233 | 204 | 20-chloro-9-oxo-3-thia-13-trans-prostenoic acid |
| 234 | 205 | 20-chloro-9-oxo-3-thia-17,18,19-trinor-13-trans-prostenoic acid |
| 235 | 206 | 9-oxo-3-thia-13-trans-17-cis-prostadienoic acid |
| 236 | 207 | 9-oxo-3-thia-19,20-dinor-13-trans-prostenoic acid |
| 237 | 219 | 9-hydroxy-3-oxa-13-trans-prostenoic acid |
| 238 | 220 | 20-chloro-9-hydroxy-3-oxa-13-trans-prostenoic acid |
| 239 | 221 | 9-hydroxy-3-oxa-13-trans-17-cis-prostadienoic acid |
| 240 | 222 | 9-hydroxy-20-methyl-3-oxa-13-trans-prostenoic acid |
| 241 | 223 | 9-hydroxy-3-thia-13-trans-prostenoic acid |
| 242 | 224 | 9-hydroxy-3-thia-13-trans-17-cis-prostadienoic acid |
| 243 | 225 | 9-hydroxy-3-thia-19,20-dinor-13-trans-prostenoic acid |
| 244 | 226 | 9-hydroxy-5-cis-13-trans-prostadienoic acid |

We claim:
1. The compounds of the formula:

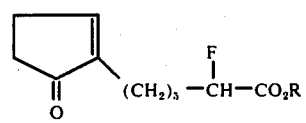

wherein R is selected from the group consisting of hydrogen and lower alkyl.

2. The compound according to claim 1 wherein R is hydrogen; 2-(6-carboxy-6-fluorohexyl)-cyclopent-2-en-1-one.

3. The compound according to claim 1 wherein R is ethyl; 2-(6-carbethoxy-6-fluorohexyl)cyclopent-2-en-1-one.

* * * * *